United States Patent
Thomsen

(10) Patent No.: US 10,281,797 B2
(45) Date of Patent: May 7, 2019

(54) LIFETIME EXTENDING AND PERFORMANCE IMPROVEMENTS OF OPTICAL FIBERS VIA LOADING

(71) Applicant: NKT PHOTONICS A/S, Birkerød (DK)

(72) Inventor: Carsten L. Thomsen, Virum (DK)

(73) Assignee: NKT PHOTONICS A/S, Birkerød (DK)

( * ) Notice: Subject to any disclaimer, the term of this patent is extended or adjusted under 35 U.S.C. 154(b) by 0 days.

(21) Appl. No.: 15/963,694

(22) Filed: Apr. 26, 2018

(65) Prior Publication Data

US 2019/0004396 A1   Jan. 3, 2019

Related U.S. Application Data

(63) Continuation of application No. 15/683,281, filed on Aug. 22, 2017, now Pat. No. 9,971,230, which is a
(Continued)

(30) Foreign Application Priority Data

Jul. 11, 2008 (DK) .................................. 2008 00985

(51) Int. Cl.
   *G02B 6/02* (2006.01)
   *B05D 3/02* (2006.01)
   (Continued)

(52) U.S. Cl.
   CPC ............. *G02F 1/365* (2013.01); *A61B 1/06* (2013.01); *G02B 6/0006* (2013.01);
   (Continued)

(58) Field of Classification Search
   CPC ........... G02F 1/365; A61B 1/06; G02B 6/006; G02B 6/02319; H01S 3/302
   See application file for complete search history.

(56) References Cited

U.S. PATENT DOCUMENTS

| 4,606,608 A | 8/1986 | Wysocki |
| 5,235,659 A | 8/1993 | Atkins et al. |

(Continued)

FOREIGN PATENT DOCUMENTS

| CA | 2 579 828 | 8/2008 |
| EP | 0 498 939 | 8/1992 |

(Continued)

OTHER PUBLICATIONS

Chen et al., "Photonic Crystal Fiber with W-Type Effective Refractive Refractive Index Profile," Optik—International Journal for Light and Electron Optics, (Aug. 2013), vol. 124, Issue 15, pp. 2309-2312.

(Continued)

*Primary Examiner* — Joseph L Williams
(74) *Attorney, Agent, or Firm* — Buchanan Ingersoll & Rooney P.C.

(57) ABSTRACT

A method of making a microstructured optical fiber including loading the core and cladding materials of the fiber with hydrogen and deuterium at a loading temperature; annealing the fiber at a selected temperature $T_{anneal}$; pumping the fiber with radiation; and reducing the temperature of the fiber and storing the fiber at the reduced temperature before the step of pumping the fiber; and wherein the method allows the hydrogen and the deuterium to become bound to the core material and the cladding material.

12 Claims, 15 Drawing Sheets

Related U.S. Application Data continuation of application No. 13/003,510, filed as application No. PCT/DK2009/050158 on Jul. 3, 2009, now Pat. No. 9,746,749.

(51) Int. Cl.
*H01S 3/00* (2006.01)
*G02F 1/365* (2006.01)
*A61B 1/06* (2006.01)
*F21V 8/00* (2006.01)
*H01S 3/30* (2006.01)
*G02B 6/42* (2006.01)
*G02B 6/44* (2006.01)
*G02F 1/35* (2006.01)

(52) U.S. Cl.
CPC ..... *G02B 6/02319* (2013.01); *G02B 6/02342* (2013.01); *H01S 3/302* (2013.01); *G02B 6/02333* (2013.01); *G02B 6/4296* (2013.01); *G02B 6/4492* (2013.01); *G02F 2001/3528* (2013.01)

(56) References Cited

U.S. PATENT DOCUMENTS

| | | | |
|---|---|---|---|
| 5,256,177 | A | 10/1993 | Bennett et al. |
| 5,267,343 | A | 11/1993 | Lyons et al. |
| 5,621,843 | A | 4/1997 | Neuberger |
| 5,802,236 | A | 9/1998 | DiGiovanni et al. |
| 5,983,073 | A | 11/1999 | Urano et al. |
| 5,983,673 | A | 11/1999 | Urano et al. |
| 6,220,059 | B1 | 4/2001 | Klein et al. |
| 6,311,524 | B1 | 11/2001 | Brennan, III et al. |
| 6,564,585 | B2 | 5/2003 | Abe et al. |
| 6,661,957 | B1 | 12/2003 | Levenson et al. |
| 6,763,686 | B2 | 7/2004 | Carpenter et al. |
| 6,944,380 | B1 | 9/2005 | Hideo et al. |
| 7,493,009 | B2 | 2/2009 | Homa |
| 8,145,023 | B2 | 3/2012 | Thomsen |
| 8,406,594 | B2 | 3/2013 | Alkeskjold |
| 9,291,770 | B2 | 3/2016 | Robin et al. |
| 9,746,749 | B2 | 8/2017 | Thomsen |
| 9,766,530 | B2 | 9/2017 | Thomsen et al. |
| 9,971,230 | B2 | 5/2018 | Thomsen |
| 2003/0215201 | A1 | 11/2003 | Tanigawa et al. |
| 2004/0057682 | A1 | 3/2004 | Nicholson et al. |
| 2005/0031867 | A1 | 2/2005 | Majid et al. |
| 2005/0226576 | A1 | 10/2005 | Feder et al. |
| 2006/0013546 | A1 | 1/2006 | Kurusu et al. |
| 2006/0188206 | A1 | 8/2006 | Majid et al. |
| 2009/0022189 | A1 | 1/2009 | Okuno |
| 2010/0040335 | A1 | 2/2010 | Thomsen |
| 2010/0266251 | A1 | 10/2010 | Lyngsoe |
| 2011/0116283 | A1 | 5/2011 | Thomen et al. |
| 2012/0195554 | A1 | 8/2012 | Maack |
| 2016/0156148 | A1 | 6/2016 | Thomsen et al. |
| 2016/0170136 | A1 | 6/2016 | Johansen et al. |
| 2017/0085051 | A1 | 3/2017 | Thomsen et al. |
| 2018/0217323 | A1 | 8/2018 | Lyngsoe et al. |

FOREIGN PATENT DOCUMENTS

| | | | |
|---|---|---|---|
| EP | 0780707 | A1 | 6/1997 |
| EP | 0 810 453 | | 12/1997 |
| EP | 0 943 936 | | 9/1999 |
| EP | 0 943 936 | A2 | 9/1999 |
| EP | 1020413 | A1 | 7/2000 |
| EP | 1 426 795 | A2 | 6/2004 |
| EP | 2 770 370 | | 8/2014 |
| EP | 2 821 379 | | 1/2015 |
| GB | 2425307 | A | 10/2006 |
| JP | S60090852 | A | 5/1985 |
| JP | H04059630 | A | 6/1990 |
| JP | 2000103629 | A | 4/2000 |
| JP | 2000137257 | A | 5/2000 |
| JP | 2002214454 | A | 7/2002 |
| JP | 2004 345919 | | 12/2004 |
| JP | 2004361526 | A | 12/2004 |
| WO | 98/57203 | A1 | 12/1998 |
| WO | 00/37974 | A1 | 6/2000 |
| WO | 02/06868 | A2 | 1/2002 |
| WO | 03/016967 | A1 | 2/2003 |
| WO | 03/078338 | A2 | 9/2003 |
| WO | 2004/095096 | A1 | 11/2004 |
| WO | WO 2005/010583 | | 2/2005 |
| WO | 2005054144 | A1 | 6/2005 |
| WO | 2006/021569 | A1 | 3/2006 |
| WO | 2008/003138 | A1 | 1/2008 |
| WO | 2008/083686 | A1 | 7/2008 |
| WO | WO 2015/003714 | | 1/2015 |
| WO | WO 2015/003715 | | 1/2015 |
| WO | WO 2015/144181 | | 10/2015 |

OTHER PUBLICATIONS

Li et al., "Interaction of Supercontinuum and Raman Solitions with Microstructure Fiber Gratings" Optics Express, 2005, vol. 13, No. 3, pp. 998-1007, XP-002474653.
Nicholson, J.W. et al., "Spatially and spectrally resolved imaging of modal content in large mode-area fibers",Optics Express, vol. 15, No. 10, pp. 7233-7243, May 12, 2008.
Extended European Search Report (Communication) dated Jun. 28, 2018, Issued by the European Patent Office in corresponding European Application No. 18158233.7-1209 (9 pages).
Extended Search Report dated Jul. 9, 2016, by the European Patent and Trademark Office in corresponding European Patent Application No. 15859379.6 (11 pages).
Search Report dated Jun. 24, 2015, by the Danish Patent and Trademark Office in corresponding Danish Patent Application No. PA 2014 70800. (9 pages).
International Search Report (PCT/ISA/210) dated Mar. 4, 2016, by the Nordic Patent Institute as the International Searching Authority for International Application No. PCT /DK2015/050395.
Written Opinion (PCT/ISA/237) dated Mar. 4, 2016, by the Nordic Patent Institute as the International Searching Authority for International Application No. PCT/DK2015/050395.
Singapore Official Action dated Jun. 19, 2018, by the Intellectual Property Office of Singapore in corresponding Singapore Patent Application No. 11201704974T (10 pages).
Office Action (Notification of Reasons for Rejection) dated Jan. 9, 2018, by the Japanese Patent Office in Japanese Patent Application No. 2016-238365, and an English Translation of the Office Action. (8 pages).
D. Griscom, "Optical Properties and Structure of Defects in Silica Glass", Journal of the Ceramic Society of Japan, 1991, pp. 923-942, vol. 99, No. 10.
F. Lu et al. "Generation of a broadband continuum with high spectral coherence in tapered single-mode optical fibers", Optics Express, Jan. 26, 2004, pp. 347-353, vol. 12, No. 2, Optical Society of America.
R. Watt et al. "Generation of supercontinuum radiation in conventional single-mode fibre and its application to broadband absorption spectroscopy", Applied Physics B, 2008, pp. 47-53, vol. 90.
M. Yuen, "Ultraviolet absorption studies of germanium silicate glasses", Applied Optics, Jan. 1, 1982, pp. 136-140, vol. 21, No. 1, Optical Society of America.
International Search Report (Form PCT/ISA/210) and Written Opinion of the International Searching Authority (Form PCT/ISA/237), dated Sep. 29, 2010, issued by the European Patent Office in corresponding International Patent Application No. PCT/DK2009/050158.
Bjarklev et al., "Photonic Crystal Fibres", Kluwer Academic Publishers, Chapter 4, 2003, pp. 115-130.
Birks et al., "2D Photonic Band Gap Structures in Fibre Form", Published in Photonic Band Gap Materials (Editor: C. M. Soukoulis) Kluwer, 1996, p. 1-8.

(56) References Cited

OTHER PUBLICATIONS

Knight et al., "All-Silica Single-Mode Optical Fiber with Photonic Crystal Cladding", Optics Letter, (1996), vol. 21, No. 19, pp. 1547-1549.
Kirchhof et al., "High-Power Stability of Optical Fibers for the Visible Wavelength Region", Proceedings of SPIE, (2001), vol. 4579, pp. 322-333, XP-002630791.
Li et al., "Electron Paramagnetic Resonance Hyperfine Spectrum of the Si E' Defect Associated with Weakly Bonded Hydrogen Molecules in Synthetic Silica Optical Fibers", Appl. Phys. Lett., (1995), vol. 66, No. 21, pp. 2816-2818.
Nagasawa et al., "Improvement of Radiation Resistance of Pure Silica Core Fibers by Hydrogen Treatment", Japanese Journal of Applied Physics, (1985), vol. 24, No. 9, pp. 1224-1228, XP-002630792.
Tomashuk et al., "γ-Radiation-Induced Absorption in Pure-Silica-Core Fibers in the Visible Spectral Region: the Effect of H2-Loading" IEEE Transactions on Nuclear Science, (1998), vol. 45, No. 3, pp. 1576-1579.
Tomashuk et al., "Radiation-Induced Absorption and Luminescence in Specially Hardened Large-Core Silica Optical Fibers" IEEE Transactions on Nuclear Science, (2000), vol. 27, No. 3, pp. 693-698, XP-002630793.
Tomashuk et al., "Radiation-Resistant and Radiation-Sensitive Silica Optical Fibers" Proceedings of SPIE, (2000), vol. 4083, pp. 188-201, XP-002630794.
Partial European Search Report dated Mar. 31, 2011, issued in the corresponding European Application No. 11 15 3488.
Office Action (Notification of Reasons for Rejection) dated Jan. 5, 2016, by the Japanese Patent Office in Japanese Patent Application No. 2015-052013, and an English Translation of the Office Action. (11 pages).
Ex parte Quayle issued on Feb. 14, 2017, by the U.S. Patent and Trademark Office in the copending U.S. Appl. No. 14/956,578. (15 pages).
The Extended European Search Report dated Mar. 29, 2012, by the European Patent Office in corresponding European Patent Application No. 11153488.9-2217. (23 pages).
Office Action (Communication pursuant to Article 94(3) EPC) dated Apr. 11, 2016, by the European Patent Office in European Patent Application No. 08 700 884.3-1903. (7 pages).
Farrow, et al. "Design of refractive-index and rare-earth-dopant distributions for large-more-area fibers used in coiled high-power amplifiers," Proceedings of the SPIE, vol. 6453, 2007, pp. 64531C-1-64531C-11.
Fu et al. "Femtosecond laser writing Bragg gratings in pure silica photonic crystal fibres" Electronics Letters, IEE Stevenage, GB, vol. 41, No. 11, May 26, 2005, pp. 638-640.
Fu, et al. "Fibre Bragg Gratings Written in Pure Silica Photonic Crystal Fibres with Ultraviolet Femtosecond Laser Pulse" 30th Australian conference on Optical Fibre Technology 2005, Jul. 4, 2005. (3 pages).
Genty, et al., "Generation of Wide Supercontinuum in a Weakly Nonlinear Microstructured Fiber," Conference on Lasers and Electro-Optics 2006, Long Beach, CA, May 2006, pp. 1-2.
Karlitschek, P., et al. "Influence of hydrogen on the colour center formation in optical fibers induced by pulsed UV-laser radiation. Part 1: all silica fibers with high-OH undoped core," Optics Communications, vol. 155, No. 4-6, Oct. 15, 1998, pp. 376-385.
Kudlinski, A., et al. "Zero-dispersion wavelength decreasing photonic crystal fibers for ultraviolet-extended supercontinuum generation," Optics Express, vol. 14, No. 12, Jun. 12, 2006, pp. 5715-5722.
Leproux, et al. "Methods for visible supercontinuum generation in doped/undoped holey fibres," Proceedings of the SPIE, vol. 6990, May 2008, pp. 699007-1-69907-4.
Stone et al., "Visibly "white" light generation in uniform photonic crystal fiber using a microchip laser," Optics Express, vol. 16, No. 4, Feb. 18, 2008, pp. 2670-2675.
Travers, J. C., et al., "High brightness polychromatic visible generation in photonic crystal fibers with picosecond Yb pumping," Lasers and Electro-Optics, 2005, (CLEO), Conference on Baltimore, MD, USA, vol. 2, May 22, 2005-May 27, 2005, pp. 1229-1230.
Travers, et al. "Extended blue supercontinuum generation in cascaded holey fibers," Optics Letters, vol. 30, No. 23, Dec. 1, 2005, pp. 3132-3134.
Unger, et al., "Transmission Behavior of Silica Core-Fluorine Doped Cladding Fibers in the Visible and Ultraviolet Region," Proceedings of the SPIE, vol. 4616, 2002, pp. 161-172.
Xiong, C., et al. "Visible continuum generation from a microchip 1062 nm laser source," Conference on Lasers and Electro-Optics and 2006 Quantum Electronics and Laser Science Conference, CLEO/QELS 2006, May 21, 2006, pp. 1-2.
Office Action dated Sep. 26, 2011, by the U.S. Patent and Trademark Office in U.S. Appl. No. 12/522,758. (9 pages).
Notice of Allowance dated Jan. 17, 2012, by the U.S. Patent and Trademark Office in the related U.S. Appl. No. 12/522,758. (8 pages).
Office Action (Communication pursuant to Article 94(3) EPC) dated Mar. 7, 2017, by the European Patent Office in corresponding European Patent Application No. 11 153 488.9-1562. (6 pages).

LIFETIME EXTENDING AND PERFORMANCE IMPROVEMENTS OF OPTICAL FIBERS VIA LOADING

CROSS-REFERENCE TO RELATED APPLICATIONS

The present application is a continuation of U.S. application Ser. No. 15/683,281, which was filed in the U.S. Patent & Trademark Office on Aug. 22, 2017, which is a continuation of U.S. application Ser. No. 13/003,510, which was filed in the U.S. Patent & Trademark Office on Jan. 10, 2011, now U.S. Pat. No. 9,746,749, which is a national stage application of PCT/DK2009/050158, which was filed on Jul. 3, 2009, and which claims the priority of Danish Patent Application No. PA 2008 00985, which was filed on Jul. 11, 2008. The contents of U.S. application Ser. No. 15/683,281; U.S. application Ser. No. 13/003,510; PCT/DK2009/050158; and Danish Patent Application No. PA 2008 00985 are incorporated herein by reference.

TECHNICAL FIELD

The invention relates specifically to an optical fiber comprising a core and a cladding comprising a core material and a cladding material, respectively.

BACKGROUND ART

Guiding of relatively high powers in an optical fiber may have relevance for several commercial applications such as guiding of surgical and/or therapeutic light, optical sensing, and materials processing. Among such applications is transport of optical energy and utilizing non-linear effects in the fiber, which are commonly more pronounced with higher optical power inside the fiber. The optical power may be continuous wave (CW), pulsed or a mixture thereof. High optical power inside a fiber may be particularly pronounced with pulsed light where a high peak power may be obtainable even while having a relatively modest average power.

One limitation of the average power/spectral density carried by an optical fiber is the damage threshold of the fiber. The input facet or the first few millimeters of fiber may be destroyed if the optical power (CW, peak power or pulse energy) is above the bulk glass or glass-air interface damage threshold. It has been observed by the present inventors that even when the optical power is below this threshold the optical fiber may still be observed to degrade over time. This degradation is often observed as increased absorption in the visible over time. For commercial applications a long lifetime may be critical.

SUMMARY

An object of the present invention is to provide a fiber where such degradation is either eliminated or reduced.

The objects of the invention are achieved by the invention described in the accompanying claims and as described in the following.

One object of the invention is achieved by an optical fiber comprising a core and a cladding comprising a core material and a cladding material, respectively, said optical fiber being obtained by a method comprising loading said core material and optionally said cladding material with hydrogen and/or deuterium under loading conditions suitable to allow hydrogen and/or deuterium to bind chemically to said material(s). In one embodiment said loading condition comprises at least one of a) a raised temperature T, b) a raised pressure P c) irradiation and/or d) subsequent irradiation. Such an optical fiber may have particular suitable properties in regard to long lifetime in applications where said fiber is arranged to guide relatively high power, such as pulsed light with relatively high peak power.

In one embodiment of the invention degradation of the fiber in a supercontinuum light source for shorter wavelengths is reduced by stripping of higher order modes. Accordingly, in one embodiment the invention relates to a supercontinuum light source comprising a fiber coupled to a pump source where said pump source and said fiber are adapted to provide an optical output spanning over at least one octave with at least 10 µW/nm, and/or wherein said pump and said fiber are adapted to provide a maximum modulation instability gain $\Omega_{max}$ larger than 20, wherein at least part of said fiber is arranged to strip higher order modes and/or suppress coupling of light from the fundamental mode to higher order modes. In one embodiment this stripping of higher order modes is combined with loading of the fiber with deuterium and/or hydrogen.

Loading by deuterium is sometimes applied in the art in order to overcome absorptions in the so-called water-band, which increases when the fiber is subjected to hydrogen-rich environments, such as found for undersea communication cables. This issue is not similar to the present problem. In one embodiment the fiber is therefore applied in an environment where it is subjected to a medium with a content of $H_2$ and/or $H^+$-ions of less than 5 at %, such as less than 1 at %, such as less than 0.1 at %, such as less than 0.01 at %, such as less than 0.001 at %.

Loading by deuterium is sometimes applied in the art in order to increase the photosensitivity of the fiber in order to enable changing its refractive index, e.g. to induce a Bragg grating in the fiber by exposure through an external light source perpendicular to the fiber. This issue is not similar to the present problem. In one embodiment the fiber is annealed prior to usage, where said anneal significantly reduces the fibers photosensitivity. In one embodiment the fiber is a pure silica fiber without dopants in which it is difficult to write Bragg gratings even if it was H2 or D2 loaded without a subsequent anneal. In one embodiment the photosensitivity of the fiber pre and/or post anneal is less than 50% of that of a typical fiber used for producing fiber Bragg gratings, such as less than 25%, such as less than 10%, such as less than 5%, such as less 1%, such as less than 0.1%, such as less than 0.001%. In one embodiment the photosensitivity is substantially zero.

In one embodiment water-band absorption (such as the peak absorption peak around 1400 nm) may be undesirable. In such an embodiment it may be preferable to load the fiber with as little hydrogen as possible so that in one embodiment the loaded fiber comprises bound deuterium relative to bound hydrogen (and/or their corresponding ions) of more than or equal to 1%, such as more than or equal to 10%, such as more than or equal to 100%, such as more than or equal to 10,000% by atom. However, hydrogen may be preferable for applications where such absorption is either insignificant or even preferable, particularly when it is noted that hydrogen is commonly significantly cheaper than deuterium. Hydrogen may also be preferable for applications where the deuterium induced OD-absorption around 1870 nm is undesirable.

In one embodiment the lifetime of a fiber has been found to increase with increased ambient temperature during loading (see FIG. 7). This dependency indicates that providing energy during loading benefits the lifetime. In one embodiment, the extended lifetime depends on a chemical process occurring between the material of the fiber and hydrogen/deuterium being loaded. In one embodiment, the lifetime has been found to increase by introducing energy subsequent to loading, such as by providing "subsequent irradiation" which is the term used throughout the application for the provision of energy to loaded material during and/or subsequent to loading. In one embodiment subsequent irradiation is taken to mean introducing energy at a rate higher than provided by the general environment subsequent to loading, i.e. energy provided by keeping the fiber at room temperature or energy provided by normal lighting is not subsequent irradiation. In one embodiment this introduction of energy stimulates the chemical process between unbound Hydrogen/Deuterium and the material. In one embodiment it is therefore preferable that subsequent stimulation comprises localized contribution of energy. In one embodiment said chemical process is binding of at least part of the loaded hydrogen and/or deuterium to the material of the fiber. In one embodiment, the fiber is being loaded by subjecting it to hydrogen and/or deuterium under loading conditions suitably to allow hydrogen and/or deuterium to bind chemically to said material(s). In one embodiment, said loading condition comprising at least one of a) raised temperature T, b) raised pressure P, c) irradiation and d) subsequent irradiation. In one embodiment the fiber is a silica fiber, so that in one embodiment said chemical process is binding of at least part of the loaded Hydrogen and/or deuterium to the silica matrix, such as forming an OH$^-$ or OD$^-$ bond. By providing such loading conditions a fiber comprising an increased amount of bound hydrogen and/or deuterium is obtainable so that in one embodiment the loaded material comprises more than 0.1 atom percent (at %) bound hydrogen and/or deuterium, such as more than 1 at %, such as more than 5 at %, such as more than 10 at %, such as more than 20 atom percent, such as more than 50 at %.

In contrast to photosensitizing of fibers via loading the temperature T is in one embodiment raised to allow for binding as discussed above, so that T is more than or equal to 80° C., such as more than or equal to 100° C., such as more than or equal to 120° C., such as more than or equal to 140° C., such as more than or equal to 160° C., such as more than or equal to 180° C., such as more than or equal to 200° C., such as more than or equal to 220° C., such as more than or equal to 240° C., such as more than or equal to 260° C., such as more than or equal to 280° C., such as more than or equal to 300° C., such as more than or equal to 350° C., such as more than or equal to 400° C., such as more than or equal to 450° C., such as more than or equal to 500° C.

The fiber may and may not comprise a coating, such as a polymer coating. In an embodiment where the fiber comprises a polymer coating the loading temperature for loading deuterium and/or hydrogen is kept below the melting point of the polymer, such as below the softening temperature of the polymer. The practical upper limit for increasing the loading temperature is likely set by the coating of the fiber. In one embodiment high temperature coating may extend the possible deuterium loading temperature to above 250° C. or even higher. One example of a high temperature coating is DeSolite® DF-0005 or DeSolite® DF-0009, manufactured by DSM Desotech Inc., which are designed for high temperature fiber applications up to about 250° C.

Alternatively, fibers without coating may be produced, allowing even higher loading temperature e.g. up to and above 500° C. and/or loading of the core (and optionally cladding) material may be performed prior or during the process of forming the fiber i.e. prior to coating. In one embodiment, the fiber is stripped of its coating and subsequently recoated.

In one embodiment the chemical reaction time depends on the temperature and/or pressure. In one embodiment the loading time during which the fiber is loaded is at least sufficient to ensure that thermal equilibrium has occurred. In one embodiment the loading time is less than 6 days, such as less than or equal to 4 days, such as less than or equal to 1 days, such as less than or equal to 1 day, such as less than or equal to 12 hours, such as less than or equal to 6 hours, such as less than or equal to 3 hours, such as less than or equal to 2 hours, such as less than or equal to 1 hours, such as less than or equal to 30 minutes, such as less than or equal to 1 minute.

An increased pressure of the loading gas may in one embodiment be utilized to provide a higher concentration of indiffused hydrogen and/or deuterium in the fiber. Also, in one embodiment the pressure P is more than or equal to 10 bars, such more than or equal to 25 bar, such more than or equal to 50 bars, such more than or equal to 75 bar, such more than or equal to 90 bar, such as more than or equal to 120 bar, such as more than or equal to 160 bar, such as more than or equal to 200 bar, such as more than or equal to 500 bar, such as more than or equal to 1000 bar, such as more than or equal to 2000 bar.

The above mentioned subsequent irradiation may in principle be any irradiation suitable for providing energy to stimulate the chemical process. In one embodiment said subsequent irradiation is light, such as light introduced during use of the fiber. In one embodiment said subsequent irradiation alters the glass structure such as by creating and/or activating defects which interact with hydrogen/deuterium. Further details of defects in glass may for example be found in the paper "OPTICAL PROPERTIES AND STRUCTURE OF DEFECTS IN SILICA GLASS" by D. L. Griscom (Journal of the Ceramic Society of Japan. Vol. 99, no. 1154, pp. 923-942, 1991). In one embodiment said irradiation is light guided by the fiber. In one embodiment light otherwise applied in use of the fiber provides the activation energy. In use of the fiber, the pump light, i.e. the light by which the fiber is pumped, entering the fiber may in one embodiment provide sufficient energy to allow unbound hydrogen/deuterium to interact with the fiber and/or create new defects with which remaining unbound hydrogen/deuterium may interact. In embodiments where the fiber is subjected to signal light and pump light or signal light alone, pump light may also refer to signal light or pump and signal light in combination. In the context of this application such subsequent irradiation of the fiber may be referred to as photo activation. However, in principle any types of irradiation of the fiber providing sufficient energy may be applied. In one embodiment UV radiation is applied as subsequent irradiation, since its higher photon energy enables chemical reactions.

In one embodiment the fiber is cooled subsequent to loading and/or annealing in order to reduce diffusion out of the fiber prior to subsequent irradiation. Accordingly, in one embodiment the fiber is stored at reduced temperature (cold storage) for a period in the time from production, i.e. loading, to subsequent irradiation. In one embodiment, reduced temperature is less than −30° C., such as less than −40° C., such as less than −50° C., such as less than −60° C., such as less than −70° C., such as less than −90° C., such as less than −100° C. In one embodiment storing at reduced temperature preserves or limits the loss of deuterium and/or Hydrogen over time. In one embodiment storing at reduced temperature is applied substantially until the fiber is put in operation. In one embodiment cold storage is applied substantially until the fiber is subjected to subsequent irradiation. In one embodiment the fiber is stored at reduced temperature after loading either before and/or after anneal. In one embodiment storing at reduced temperature is applied at least part of the time between loading and/or anneal and subsequent irradiation and/or operation. In one embodiment the fiber is subjected to storing at reduced temperature during operation.

In one embodiment the term subsequent in subsequent irradiation, e.g. photo activation, refers to a maximum time between loading and subsequent irradiation less than or equal to 2 months, such as less than or equal to 1 month, such as less than three weeks, such as less than or equal to 14 days, such as less than or equal to 7 days, such as less than or equal to 4 days, such as less than or equal to 1 day, such as less than or equal to 12 hours, such as less than or equal to 6 hours, such as less than or equal to 3 hours, such as less than or equal to 1 hour, such as less than or equal to 1 minute. If the maximum time between loading and subsequent irradiation is exceeded, this will in one embodiment lead to that the lifetime extension effect of the loading is decreased relative to subjecting the fiber to irradiation immediately after loading. In one embodiment storing the fiber at reduced temperature significantly reduces the effects which cause this decrease in lifetime. In one embodiment the time where the fiber has been stored at reduced temperature is therefore not counted in the calculation of the maximum time as described above. In other words, maximum time between loading and subsequent irradiation refers in one embodiment to a maximum accumulated time, not counting time wherein said fiber has been stored at reduced temperature, between loading and subsequent irradiation of less than 2 months, such as less than 1 month, such as less than 14 days, such as less than 7 days, such as less than 4 days, such as less than 1 day, such as less than 12 hours, such as less than 6 hours, such as less than 3 hours, such as less than 1 hour, such as less than 1 minute. In one embodiment the term stored refers to the fiber not being used while in storage, whereas in one embodiment stored refers to the fiber being in use while in storage.

In one embodiment subsequent irradiation is performed by irradiation of the fiber by applying irradiation transversely to the optical axis. In one embodiment subsequent irradiation is performed by applying irradiation to an end facet of the fiber, such as by coupling light or other radiation into the fiber. In one embodiment said irradiation is side coupled to the fiber. In one embodiment the fiber is subjected to subsequent irradiation prior to annealing the fiber. In one such embodiment the fiber ends of the fiber may be annealed to allow splicing of the fiber. In one embodiment said light is coupled into the fiber by splicing the fiber to a light source of delivery fiber. In one embodiment light is coupled into the fiber via free-space or butt-coupling.

In one embodiment subsequent irradiation, e.g. photo activation, comprises pumping the fiber with light having a peak power density within said fiber equal to or higher than 10 W/$\mu$m$^2$, such as equal to or higher than 50 W/$\mu$m$^2$, such as equal to or higher than 100 W/$\mu$m$^2$, such as equal to or higher than 500 W/$\mu$m$^2$, such as equal to or higher than 1 kW/$\mu$m$^2$, such as equal to or higher than 2.5 kW/$\mu$m$^2$, such as equal to or higher than 5 kW/$\mu$m$^2$, such as equal to or higher than 10 kW/$\mu$m$^2$. In one embodiment the subsequent irradiation comprises pumping said fiber with irradiation having an average power of 50 mW or more, such as 100 mW or more, such as 500 mW or more, such as 1 W or more, such as more than 10 W or more, such as 15 W or more, such as 20 W or more, such as 50 W or more, such as 100 W or more. In one embodiment the subsequent irradiation has a duration of more than $\frac{1}{1000}$ of a second, such as more then $\frac{1}{100}$ of a second, such as more than $\frac{1}{10}$ of a second, such as more than 1 second, such as more than 1 minute, such as more than 1 hour, such as more than 12 hours, such as more than 24 hours, such as more than 48 hours, such as more than 1 week.

In principle the materials may be loaded at any time in the process of forming the fiber. However, consideration may have to be taken to ensure that processes following the loading do not disrupt the achieved extension of the lifetime of the final fiber. Such a disruption may occur if a process following the loading comprises conditions which allow the loaded hydrogen/deuterium to escape from the fiber e.g. a sufficiently high temperature over a sufficiently long time. Accordingly, in one embodiment the loading of the core material, and optionally of said cladding material, being performed prior to forming said fiber, during forming of said fiber and/or after forming said fiber. Furthermore, as shown in FIG. 5 discussed below, fibers may, at least partially, be regenerated so that in one embodiment the fiber is loaded after use.

After deuterium and/or hydrogen loading, the fiber is preferably annealed. The anneal enables splicing the fiber to other fibers (plasma heating of hydrogen/deuterium, such as in fusion splicing, may be explosive) and reduces any added photosensitivity due to these molecules. However, as discussed below, an anneal may also serve other functions such as providing increased lifetime of the fiber and increased spectral stability of embodiments of supercontinuum light sources according to the invention. Furthermore, in one embodiment the fiber is annealed prior to loading of the fiber, such as to relieve defects or stress in the fiber material. In one embodiment the fiber is anneal as a part of the drawing process. In one embodiment fiber is annealed between pulling the fiber and coating of the fiber. In one embodiment the temperature of this anneal is equal to or less than the temperature applied to the preform when pulling the fiber, such as 90% or less of that temperature, such as 80% or less of that temperature, such as 70% or less of that temperature, such as 60% or less of that temperature, such as 50% or less of that temperature, such as 40% or less of that temperature, such as 30% or less of that temperature, such as 20% or less that temperature, such as 10% or less that temperature. In one embodiment the anneal is a flash anneal providing a relatively brief high energy irradiation.

In one embodiment excessive anneal temperature above approximate 1000° C. may lead to out diffusion of the bound hydrogen/deuterium and is therefore often undesirable. In one embodiment the anneal is performed for more than 30 minutes, such as more than 1 hours, such as more than 4 hours, such as more than 8 hours, such as more than 16 hours, such as more than 32 hours, such as more 64 hours. In one embodiment the anneal is a flash anneal of the fiber with or without coating. In one embodiment said anneal is performed at a temperature T$_{anneal}$ of more than 40° C., such as more than 50° C., such as more than 60° C., such as more than 70° C., such as more than 80° C., such as more than 90° C., such as more than 100° C., such as more than 110° C., such as more than 120° C., such as more than 130° C., such as more than 140° C., such as more than 150° C., such as more than 160° C., such as more than 200° C., such as more than 250° C., such as more than 300° C., such as more than 350° C., such as more than 450° C., such as more than 550° C. In one embodiment the anneal is performed in a chamber comprising an atmosphere adapted to be less aggressive with respect to the materials of the fiber, such as its coating, relative to atmospheric air. Surrounding the fiber with such an atmosphere during the anneal may provide a reduction in damage to the fiber and/or its coating due to the raised temperature relative to atmospheric air. In one embodiment said atmosphere of the chamber comprises a mixture of gasses that have low tendency to interact chemically with the optical fiber and/or its coating. In one embodiment the anneal is performed in an atmosphere which is essentially free of oxygen or other free radicals. In one embodiment the anneal is performed in an atmosphere substantially formed by Nitrogen, Argon, an inert gas, or a mixture thereof.

In one embodiment the anneal is performed in the same chamber that is used for loading. In one embodiment the fiber is subjected to subsequent irradiation during the anneal. In one embodiment the fiber is exposed to a flash irradiation in the chamber. In one embodiment the irradiation is coupled into the fiber such as by irradiating the fiber end inside or outside the chamber. In one embodiment a piece of transport fiber is spliced to the fiber to allow the entire fiber to reside in the chamber. In one embodiment the fiber end which the transport fiber is spliced to is annealed sufficiently to allow splicing. In one embodiment the irradiation is a general irradiation of at least part of the fiber surface such as via a light source in the chamber and/or through a window in the chamber.

In one embodiment the lifetime of the fiber is extended relative to the lifetime of an otherwise identical fiber not subjected to loading by deuterium and/or hydrogen by more than 50%, such as more than 100%, such as more than 200%, such as more than 500%, such as more than 1000%, such as more than 10.000%. The absolute lifetime of a fiber subjected to light suitable for generating a supercontinuum may vary depending on the application as well as on the particular material of the fiber core. In one embodiment the lifetime is more than 100 operating hours, such as more than 200 operating hours, such as more than 2000 operating hours, such as more than 20000 operating hours, such as more than 50000 operating hours.

In one embodiment the lifetime of a fiber has been found to scale inversely with the peak power of the guided light to the fourth power. Accordingly, in such embodiment a reduction of the peak power by a factor of 2 may extend the lifetime of the fibre by a factor 16.

In one embodiment the lifetime is measured after an initial burn out time of more than 1 minute, such as more than 1 hour, such as more than 5 hours, such as more than 10 hours, such as more than 15 hours, such as more than 20 hours, such as more than 24 hours, such as more than 2 days, such as more than 7 days. In one embodiment, an initial burn out time was observed to impose a decrease of 10% of the spectrum in the visible emitted by a supercontinuum light source. In this context "burn out time" is understood as an initial time of operation where after the system/fiber/light source reaches a steady state operation. In this context steady state is taken to mean that performance changes are slow relative to the performance change during the burn out time, such as at least 50% or lower, such as at least 100% slower, such as at least 300% slower. In one such example a laser has an output power which increases 2% and thereafter reduces about 10% during the initial two days of operation after which it has a 2% reduction of output power during the next 100 days of operation all else maintained equal. In such an example "burn out time" may be defined as the first two days of operation. In one embodiment lifetime could be defined relative to the initial output power and in one embodiment relative to the maximum output power and in one embodiment relative to the output power after two days of operation.

In one embodiment the lifetime of a fiber is defined as time in which the fiber may be operated according to its operational purpose. In one embodiment the lifetime of a fiber is defined as the time after which the absorption has increased by more than or equal to 1%, such as more than or equal to 5%, such as more than or equal to 10%, such as more than or equal to 20%, such as more than or equal to 30%, such as more than or equal to 40%, such as more than or equal to 50%, such as more than or equal to 100%, such as more than or equal to 200%, such as more than or equal to 500%, such as more than or equal to 1000%. In one embodiment said fiber forms part of a light source or another system emitting light. In one such embodiment the lifetime of the fiber is defined as the time after which the optical output power of the light source or system is reduced by more than or equal to 1% all else equal, such as more than or equal to 5%, such as more than or equal to 10%, such as more than or equal to 20%, such as more than or equal to 30%, such as more than or equal to 40%, such as more than or equal to 50%, such as more than or equal to 60%, such as more than or equal to 70%, such as more than or equal to 80%, such as more than or equal to 90%. In one embodiment the optical output of said light source and/or system emitting light is pulsed, in which case the optical output power may be taken to be the peak power, average power and/or pulse power. In one embodiment the optical output power relates to the contribution of pump energy to the light source and/or system emitting light either via optical power (such as via a pump laser) or electrically or by other means. In one embodiment the lifetime is defined as more than or equal to a 1% increase in pump energy that is required to maintain the same optical output power, such as more than or equal to 5%, such as more than or equal to 10%, such as more than or equal to 20%, such as more than or equal to 30%, such as more than or equal to 40%, such as more than or equal to 50%, such as more than or equal to 100%, such as more than or equal to 200%, such as more than or equal to 500%, such as more than or equal to 1000%. In one embodiment said absorption or reduction of optical power output increase is within more than or equal to 1% of the range of wavelengths for which the fiber/system/light source is operated, such as more than or equal to 5%, such as more than or equal to 10%, such as more than or equal to 20%, such as more than or equal to 30%, such as more than or equal to 40%, such as more than or equal to 50%, such as more than or equal to 60%, such as more than or equal to 70%, such as more than or equal to 80%, such as more than or equal to 90%.

The amount of bound deuterium and/or hydrogen may in one embodiment be determined by spectroscopy. In one embodiment, such determination comprises determining the height of the absorption peak around 1380 nm of the Oft bond and/or the absorption peak at 1870 nm of the OD⁻ bond. As the absorption cross sections of these bonds are known the measured peak height may in one embodiment be used to determine the concentration of such bonds. In one embodiment said peak(s) may be applied to determine an overrepresentation of hydrogen and/or deuterium relative to an unloaded fiber. In one embodiment, the amount of bound deuterium and/or hydrogen may be determined by spectroscopy of the UV spectrum particularly around 240 nm. As glass is highly absorbent in this region only a fairly short fiber may often be investigated at a time. Further details of such measurements may be found in M. J. Yuen, "Ultraviolet absorption studies of the germanium silicate glasses", Appl. Opt., Vol. 21, 1, 1982, pp. 136-140.

In one embodiment, an over representation of bound deuterium relative to an unloaded fiber, consistent with loading of the fiber according to invention, may be determined at least partially by secondary ion mass spectroscopy (SIMS). In one such embodiment the amount of OD$^-$ is determined. In one embodiment the amount of SiD$^-$ is determined as the measurement chamber may comprise gaseous oxygen whereas there is commonly little or no gaseous silicium in the measurement chamber. In one embodiment the determination is performed relative to an unloaded fiber as variations in isotope concentration etc. may be cancelled.

In one embodiment determination of whether a fiber has been loaded according to the invention is performed by observing changes in the lifetime of the fiber pre and post an anneal designed to reduce bound deuterium and/or hydrogen. In one embodiment the fiber is annealed at a temperature where the stability of the components of the fiber, such as the coating, is ensured while the duration of the anneal may be determined by this temperature and the knowledge of the activation energy for breaking the bond in question. A drop in lifetime due to the specially designed anneal is consistent with a loading of the fiber according to the invention. Such a drop in lifetime may be a change in absorption spectrum or a change in the emission spectrum for a supercontinuum light source (such as discussed below).

In one embodiment the optical fiber is a non-linear optical fiber. In one embodiment a non-linear fiber is taken to mean a fiber which guides light for at least a range of wavelengths $\lambda_{min}$ to $\lambda_{max}$ and has a non-linear parameter $\gamma$, wherein for at least part of said range the product $\gamma \cdot \lambda$, is more than or equal to $4 \cdot 10^{-9}$ W$^{-1}$, such as more than or equal to $5 \cdot 10^{-9}$ W$^{-1}$, such as more than or equal to $6 \cdot 10^{-9}$ W$^{-1}$, such as more than or equal to $7 \cdot 10^{-9}$ W$^{-1}$, such as more than or equal to $8 \cdot 10^{-9}$ W$^{-1}$, such as more than or equal to $10 \cdot 10^{-9}$ W$^{-1}$, such as more than or equal to $20 \cdot 10^{-9}$ W$^{-1}$, such as more than or equal to $40 \cdot 10^{-9}$ W$^{-1}$. The non-linear parameter $\gamma$ is defined as $$\gamma = \frac{2\pi}{\lambda} \frac{n_2}{A_{eff}},$$

where here $n_2$ is the nonlinear refractive index of the fiber material and $A_{eff}$ is the effective mode area of the fiber. As an example, $n_2$ is commonly approximately $2.6 \cdot 10^{-20}$ m$^2$/W for silica glass.

In one embodiment a non-linear fiber is taken to mean a fiber having a non-linear parameter $\gamma$ when guiding a wavelength of 1550 nm wherein $\gamma$ is more than or equal to $3 \cdot 10^{-3}$ (Wm)$^{-1}$, such as more than or equal to $5 \cdot 10^{-3}$ (Wm)$^{-1}$, such as more than or equal to $10 \cdot 10^{-3}$ (Wm)$^{-1}$, such as more than or equal to $15 \cdot 10^{-3}$ (Wm)$^{-1}$, such as more than or equal to $20 \cdot 10^{-3}$ (Wm)$^{-1}$, such as more than or equal to $30 \cdot 10^{-3}$ (Wm)$^{-1}$, such as more than or equal to $40 \cdot 10^{-3}$ (Wm)$^{-1}$, such as more than or equal to $50 \cdot 10^{-3}$ (Wm)$^{-1}$.

In one embodiment a non-linear fiber is taken to mean a fiber having a non-linear parameter $\gamma$ when guiding a wavelength of 1064 nm wherein $\gamma$ is more than or equal to $5 \cdot 10^{-3}$ (Wm)$^{-1}$, such as more than or equal to $10 \cdot 10^{-3}$ (Wm)$^{-1}$, such as more than or equal to $15 \cdot 10^{-3}$ (Wm)$^{-1}$, such as more than or equal to $20 \cdot 10^{-3}$ (Wm)$^{-1}$, such as more than or equal to $30 \cdot 10^{-3}$ (Wm)$^{-1}$, such as more than or equal to $40 \cdot 10^{-3}$ (Wm)$^{-1}$, such as more than or equal to $50 \cdot 10^{-3}$ (Wm)$^{-1}$.

In one embodiment a non-linear fiber is taken to mean a fiber where said fiber guide light for at least a range of wavelengths $\lambda_{min}$ to $\lambda_{max}$ and a mode field diameter (MFD) of the fundamental mode least part of said range the fraction MFD/$\lambda$ is less than or equal to 5, such as less than or equal to 4, such as less than or equal to 3, such as less than or equal to 2, such as less than or equal to 1.

In the above embodiments the range of wavelengths $\lambda_{min}$ to $\lambda_{max}$ may be selected from the group of 350 nm to 2000 nm, 980 nm to 1550 nm, 1100 to 1550 nm, 1300 nm to 1450 nm, 1500 nm to 4000 nm, 1500 nm to 6000 nm, 1500 nm to 11000 nm. In one embodiment $\lambda_{min}$ is more than or equal to 300 nm, such as more than or equal to 350 nm, such as more than or equal to 450 nm, such as more than or equal to 600 nm, such as more than or equal to 750 nm, such as more than or equal to 900 nm, such as more than or equal to 1050 nm, such as more than or equal to 1200 nm, such as more than or equal to 1350 nm, such as more than or equal to 1500 nm, such as more than or equal to 2000 nm, such as more than or equal to 3000 nm. In one embodiment $\lambda_{max}$ is less than or equal to 11000 nm, such as less than or equal to 10000 nm, such as less than or equal to 8000 nm, such as less than or equal to 5000 nm, such as less than or equal to 2500 nm, such as less than or equal to 2000 nm, such as less than or equal to 1500 nm, such as less than or equal to 1000 nm, such as less than or equal to 800 nm, such as less than or equal to 600 nm, such as less than or equal to 500 nm. In one embodiment the range of wavelengths $\lambda_{min}$ to $\lambda_{max}$ is selected so as to limit the consideration to the range of wavelengths wherein the fiber is single mode.

In one embodiment a non-linear fiber is taken to mean a fiber having an MFD when guiding a wavelength of 1550 nm wherein said MFD is less than or equal to 10 μm, such as less than or equal to 8 μm, such as less than or equal to 6 μm, such as less than or equal to 5 μm, such as less than or equal to 4 μm, such as less than or equal to 3 μm, such as less than or equal to 2 μm, such as less than or equal to 1 μm.

In one embodiment a non-linear fiber is taken to mean a fiber having an MFD when guiding a wavelength of 1064 nm wherein said MFD is less than or equal to 6 μm, such as less than or equal to 5 μm, such as less than or equal to 4 μm, such as less than or equal to 3 μm, such as less than or equal to 2 μm, such as less than or equal to 1 μm.

In a preferred embodiment the fiber is a silica fiber, wherein at least a part of the core being of silica or doped silica, preferably at least the entire core being of silica or doped silica, such as the entire core and part or all of the cladding being of silica or doped silica.

In one embodiment the fiber is at least partly made of glass from the group of soft glasses, such as e.g. fluoride classes (such as e.g. ZBLAN, Fluorozirconate, Fluoroindate, Fluoroaluminate or Fluorogallate) or a chalcogenide (such as sulphide, selenide, and telluride and the IRT-SU product family offered by Corative) This embodiment may be particularly suitable for applications where the wavelengths range comprises wavelengths larger than 2 μm. In one embodiment it might be preferable to load with hydrogen instead of deuterium to avoid the OD absorption peak around 1870 nm that may otherwise arise.

In one embodiment the invention relates to an optical system comprising an optical fiber according to the invention and a feeding unit wherein said feeding unit is adapted to feed said fiber with light with a peak power density within said fiber equal to or higher than 10 W/μm$^2$, such as equal to or higher than 50 W/μm$^2$, such as equal to or higher than 100 W/μm$^2$, such as equal to or higher than 500 W/μm$^2$, such as equal to or higher than 1000 W/μm$^2$, such as equal to or higher than 2500 W/μm², such as equal to or higher than 5.000 W/μm², such as equal to or higher than 10.000 W/μm². Application where such high peak power density in the fiber are in the present document referred to as high power applications. It should be noted, that while reference is made to peak power which commonly is a feature of pulsed light, peak power may in this context refer to CW light as well.

In one embodiment said feeding unit comprises a pump light source and in one embodiment the feeding unit also comprises one or more amplifiers. In principle the feeding unit may be any optical system feeding light to the fiber.

As the fiber according to the invention has no or reduced degradation due to exposure to high peak power such a system may have an extended lifetime of operation depending on the significance of the fiber performance and life-time relative to that of other components in the system.

In one aspect the invention relates to a method of producing an optical fiber comprising a core and a cladding comprising a core material and a cladding material, respectively, said fiber having extended lifetime in high power applications, the method comprising a. loading said core material and optionally said cladding material with hydrogen and/or deuterium
b. optionally annealing said for a time $t_{anneal}$ at a temperature $T_{anneal}$.

Such a method may be advantageously applied to produce a fiber according to the invention and any features described in relation to features of the fiber may apply mutatis mutandis to the method of producing the fiber.

In one embodiment the said loading is performed by subjecting the core material and/or the cladding material to hydrogen and/or deuterium under loading conditions suitable to allow hydrogen and/or deuterium to bind chemically to said material(s). In one embodiment the said loading is performed by subjecting the core material and/or the cladding material to hydrogen and/or deuterium under loading conditions comprising at least one of a) a raised temperature T, b) a raised pressure P c) irradiation and/or d) subsequent irradiation.

In an embodiment the invention relates to an apparatus comprising an optical fiber according to the invention, an optical system according to the invention, a light source according to the invention and/or a fiber produced according to the invention. In one embodiment the apparatus constitutes a system for performing one from the group of laser precision spectroscopy, various forms of fluorescent microscopy, guiding of surgical and/or therapeutic light, astronomy (guide star generation), confocal microscopy endoscopy, optical coherence tomography (OCT) and combinations thereof.

As mentioned above, it has been found that it is often possible to regenerate a degenerated fiber, thus providing a fiber with extended lifetime compared to an identical fiber not subjected loading. Accordingly, in one embodiment the invention relates to a method of regenerating a fiber comprising a core and a cladding comprising a core material and a cladding material, respectively, said fiber having increased absorption in the visible due to subjection to light in a high power application the method comprising loading the fiber with hydrogen and/or deuterium. In one embodiment loading of said fiber is carried out under loading conditions allowing hydrogen and/or deuterium to bind to the core material and/or a cladding material. In one embodiment loading of said fiber is carried out under loading conditions comprising at least one of a) a raised temperature T, b) a raised pressure P c) irradiation and/or d) subsequent irradiation. Furthermore, any features described in relation to loading of the fiber prior to use discussed above may in one embodiment apply mutatis mutandis to the method of producing the fiber.

It should be emphasized that the term "comprises/comprising" when used in this specification is taken to specify the presence of stated features, integers, steps or components but does not preclude the presence or addition of one or more other stated features, integers, steps, components or groups thereof.

BRIEF DESCRIPTION OF DRAWINGS

The invention will be explained more fully below in connection with preferred embodiments and with reference to the drawings in which.

Figure 14:
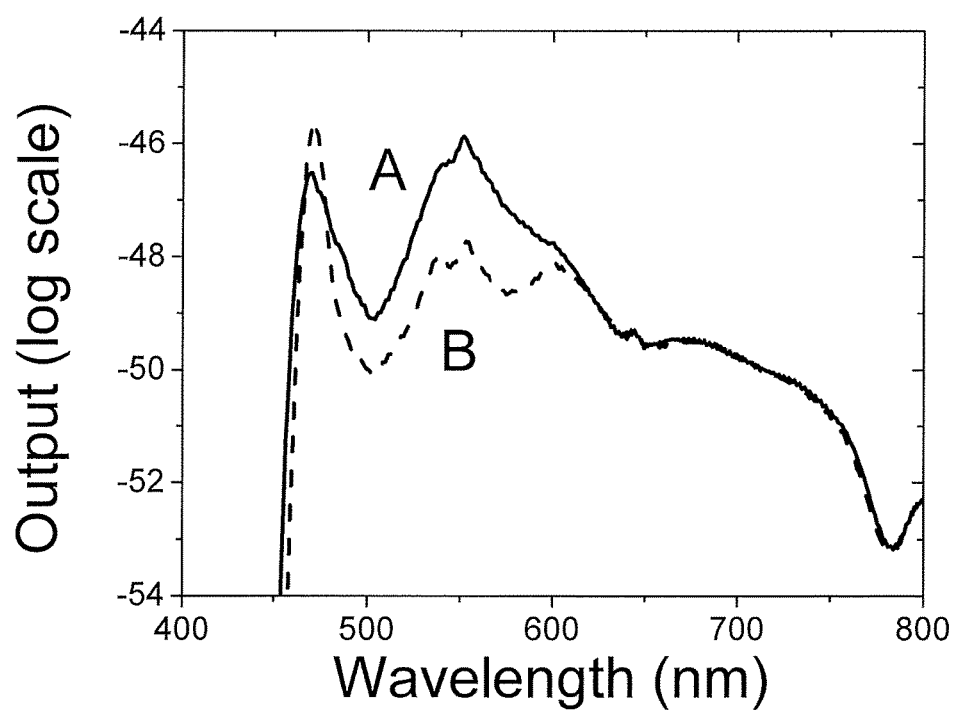
Figure 15:
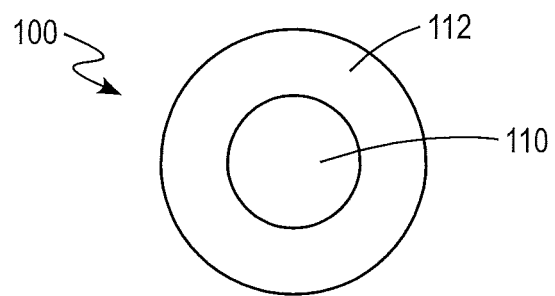

C in an atmosphere of nitrogen. The spectra are an initial spectrum (A) and a spectrum after 3500 hours of operation where the fiber has degraded in the visible region (B);

FIG. 14 shows spectra obtained from a supercontinuum source according to the invention after 3200 hours of operation. The microstructured fiber has been annealed for 4 hours at 160 C in an atmosphere of nitrogen. The spectra A is for a supercontinuum source with an uncoiled loaded nonlinear fiber according to invention, whereas in B, the nonlinear fiber is coiled with a radius of 25 mm; and FIG. 15 is a schematic cross-sectional view of an optical fiber according to an embodiment of the invention. The drawing is not made to scale, and is not intended to illustrate the relative diameters and thicknesses of the core material and cladding.

Further scope of applicability of the present invention will become apparent from the detailed description given hereinafter. However, it should be understood that the detailed description and specific examples, while indicating preferred embodiments of the invention, are given by way of illustration only, and should not be taken to limit the inventions as set forth by the appended set of claims.

DETAILS OF THE INVENTION

In the following some examples will comprise discussion of the invention based on measured data. The conclusions drawn from these should not necessarily be considered limited to the specifics of the underlying experiments.

Super Continuum Generation in Microstructured Fibers

In one embodiment, of the invention the optical fiber is a microstructured optical fiber. Microstructured optical fibers are a relatively new technical field where the properties of the waveguide may be designed with a relatively large degree of freedom. Such fibers are commonly made of pure silica comprising a pattern, often made of holes or doped glass, extending in the longitudinal direction of the fiber. The freedom of design makes such fibers interesting for application requiring specific non-linear properties of the fiber. One such application is supercontinuum generation wherein a fiber based source is cable of generating a wide spectral output. Supercontinuum (SC) generation in microstructured fibers has been studied for several years as a source of broadband light (termed white light or supercontinuum). While new applications of such sources are continuously discovered, several have already been identified, such as various forms of fluorescent microscopy, laser precision spectroscopy, and optical coherence tomography (OCT). High brightness emission in the visible part of the spectrum is especially important for confocal fluorescent microscopy. SC-generation with relatively high power in the visible has been targeted in the experiments presented here. Most research has so far been based on seeding the microstructured fiber with femtosecond (fs)-lasers but SC-generation using nanosecond- and picosecond (ps)-lasers has also been demonstrated.

As microstructured fibers often guides by holes extending in the cladding such fibers often consist entirely of un-doped silica (i.e. both core and cladding are made of silica) in opposition to e.g. standard single mode communication fibers where the core is commonly doped with germanium in order to change the refractive index. Accordingly, in one embodiment the core of the fiber comprises a Germanium content of less than or equal to 20 at %, such as less than 5 at %, such as less than 3 at %, such as less than 2 at %, such as less than 0.1 at %, such as less than 0.01 at %, such as less than 0.001 at %.

In one embodiment, submitting the fiber to subsequent irradiation may significantly improve the lifetime of the fiber. In one embodiment experimental results have shown a reduction of optical power of a supercontinuum light source of 30% after 40 hours of operation when the fiber has not been loaded, 30% after 80 hours when the fiber has been loaded and the ends subsequently sealed and the fiber stored at room temperature for over 1 month and only 4% after 200 hours when the fiber was loaded and photo activated within 1 week of load with the ends sealed. It may be noted that in one embodiment experiments have shown that the above degradation scales with applied peak power to the fourth power. Accordingly, the above periods may in one embodiment be extended by e.g. a factor of 16 by reducing the applied optical peak power with 50%. In one embodiment the latter result was found to drop approximately 10% over the first 24 hours where after the source showed this stability.

Figure 10:
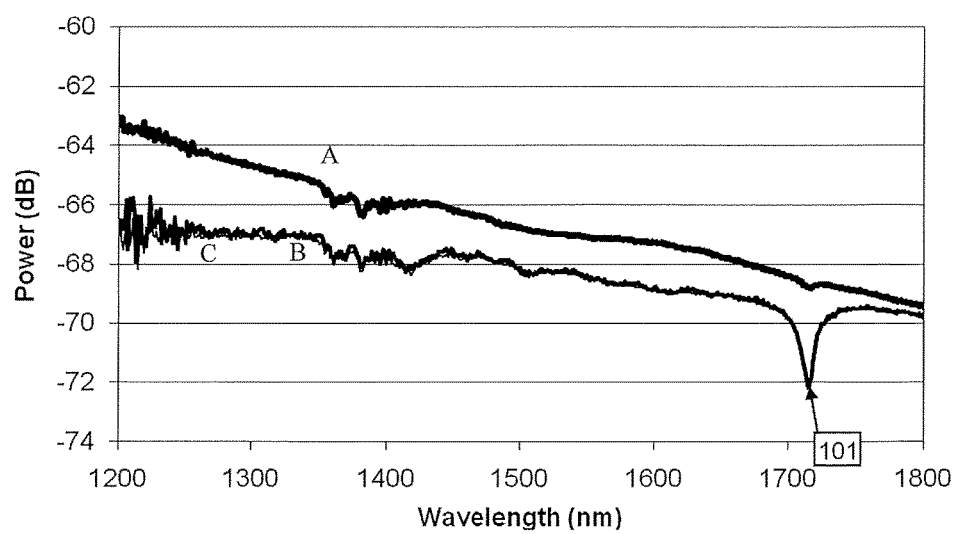
FIG. 10 shows results from a transmission experiment involving a microstructed fibre, showing the transmission just post loading (C), and 22 hours after loading where the ends of the fiber has been sealed (B). For comparison, a transmission curve is shown for a similarly loaded microstructured with unsealed fiber ends 2.5 hours post loading (A)

In one embodiment, the application of irradiation of the fiber subsequent to loading utilizes gaseous hydrogen/deuterium residing in the microstructures formed by holes of a microstructured fiber. In one embodiment the fiber is annealed to improve the life time of the fiber and/or to allow splicing of the end, such as discussed above. However in one embodiment it may be preferable to allow gaseous hydrogen/deuterium to reside in the holes of the microstructure just prior to or during subsequent irradiation, such as photo activation. In such embodiments it may be preferable to seal one or both ends of the fiber. Said sealing is performed prior to storage at reduced temperature and/or prior to loading. In one embodiment sealing is performed by supplying sufficient thermal power, such as by an arch or fusion splicer. In one embodiment sealing is performed by applying a resin, such as epoxy to the fiber ends. In one embodiment said resin may be UV cured. As shown in FIG. 10, the initial absorption shown by the dip in transmission around 1710 nm (101) is substantially unchanged for a fiber just after loading (B) and 22 hours post loading with sealed ends (C). On the other hand the same peak is shown to be substantially gone after just 2.5 hours when the ends are left unsealed (A). In some embodiments of the invention the application of such microstructured fibers is selected from the group of supercontinuum generation, optical power transport, optical amplification and forming part of a laser cavity. It is preferred that the irradiation is performed subsequent to loading; however, in one embodiment, it is performed during loading.

In one embodiment sealing of the fiber ends may be preferable to minimize the entrance of impurities into the fiber via the microstructures. In one embodiment such impurities comprises water, which may condensate on the fiber post having the fiber stored at reduced temperature. In one such embodiment said water may otherwise travel to the inside of the fiber via capillary forces and/or diffusion.

As will be apparent to the skilled person, the considerations in regard to gaseous hydrogen/deuterium in the microstructures and the sealing of these may in one embodiment be relevant for applications of microstructured fibers other than super continuum generation, such as power delivery.

In one embodiment the invention relates to a supercontinuum light source comprising a pulsed pump light source and an optical fiber according to the invention wherein said pump source is adapted to provide light with a peak power density within said fiber equal to or higher than 10 W/$\mu$m$^2$, such as equal to or higher than 50 W/$\mu$m$^2$, such as equal to or higher than 100 W/$\mu$m$^2$, such as equal to or higher than 0.5 kW/µm², such as equal to or higher than 1 kW/µm², such as equal to or higher than 2.5 kW/µm², such as equal to or higher than 5 kW/µm², such as equal to or higher than 10 kW/µm², and/or wherein said pump and fiber is adapted to provide an output spanning over at least one octave with at least 10 µW/nm and/or wherein said pump and said fiber is adapted to provide a maximum modulation instability gain $\Omega_{max}$ such as larger than 20, such as larger than 40.

Here the modulation instability gain $\Omega_{max}$ is given by $$\Omega_{max} = \pm\sqrt{\frac{2\gamma P_{peak}}{|\beta_2|}},$$

where $\beta_2$ is the group velocity at the pump wavelength, $P_{peak}$ is the peak power of the pump and $\gamma$ is the pump wavelength.

In one example more than one octave span has been achieved with the microstructured nonlinear fiber SC-5.0-1040 from the Danish company Crystal Fiber A/S. Using this fiber with a peak power of 200 W pumped at 1064 nm provided $\Omega_{max}$=22 (A peak power of 200 W is e.g. obtained through a 50 MHz, 100 mW input signal with 10 ps pulses).

In one embodiment the pump light source comprises a laser which may be pulsed or continuous wave. The laser may in principle be any suitable laser to provide the desired wavelength(s), power and/or temporal performance (i.e. pulse length, repetition rate etc.). In one embodiment said laser is a fiber laser, such as a mode locked fiber laser. In one embodiment the pump light source further comprises one or more amplifiers arranged to amplify the output of said laser. In one such embodiment the laser light source is formed by a so-called MOPA configuration.

The phrase spanning over at least one octave with at least a specific power value (per nm wavelength) is in this context of the present invention taken to mean that the optical spectrum of the output of the light source spans at least an octave defining the outer limits of said spectrum by said specific power value. The spectrum may have holes; however, it is assumed that more than 25% of the spanned spectrum has at least the specific power value. In an embodiment at least 30% of the spanned spectrum has at least the specific power value, such as at least 40%, such as at least 60%, such as at least 80%, such as at least 99%, such as at least 99.9%.

In one embodiment, the output spans over at least one octave with at least 50 µW/nm, such as more than or equal to 500 µW/nm, such as more than or equal to 1 mW/nm, such as more than or equal to 5 mW/nm, such as more than or equal to 10 mW/nm. Depending on the chosen power limit one embodiment may also span over more than or equal to 0.5 octave, such as more than or equal to 1.5 octave, such as more than or equal to 2 octaves.

In one embodiment the spectral degradation of a supercontinuum light source light comprising a non-linear microstructured fiber is less than 5% over more than 50 hours, such as over more than 100 hours, such as over more than 500 hours, such as over more than 1000 hours. In one embodiment the light system with which the light source is made to interact is recalibrated at least every 1000 hours, such as at least every 500 hours, such as at least every 100 hours, such as at least every 50 hours. In one embodiment anneal of the fiber is preferred in order to improve the spectral stability.

In one embodiment the non-linear fiber is polarization maintaining (PM) as this in one embodiment may provide a similar spectrum with a 50% reduction of the necessary peak power. In one embodiment the degradation scales with the applied peak to the fourth power so that a significant extension of the lifetime of the fiber and thereby the light source may be available. In one embodiment this requires a good polarization extinction ratio of the feed system pumping the non-linear fiber, such as more than 10 dB, such as more than 13 dB, such as more than 15 dB, such as more than 17 dB, such as more than 20 dB.

In one embodiment the non-linear fiber and the feed system, i.e. feeding unit, are coupled using bulk optics. However, as a bulk optic coupling system may provide many degrees of freedom and is often prone to mechanical and thermal instability splicing of the two components may be preferred. In one embodiment the feed system is spliced to the non-linear fiber. In one embodiment the feed system comprises an optical amplifier providing the output of the feed system into the non-linear fiber. In one embodiment there is a significant mismatch in core size between the feed system (e.g. a diameter of 11 µm) and the non-linear fiber (e.g. a diameter of 3 µm). In one embodiment this mismatch is reduced by allowing the core of the non-linear fiber to expand during splicing.

In the following measured data were obtained for a supercontinuum light source comprising a pump source and a non-linear microstructured silica fiber. The fiber was pumped at 1064 nm with 8 ps pulses at a repetition rate of 80 MHz providing a 15 W input average power (23 kW peak power). The fiber had a mode field diameter of 3.5 µm, and air-filling fraction of about 50% and was approximately 7 meters in length. The pump light source was formed by a master-oscillator power amplifier (MOPA) design comprising a mode-locked laser, a preamplifier and a power amplifier followed by two pre-amplifiers.

The length of the fiber is preferably kept short to keep the consumption of fiber to a minimum while still providing sufficient length to allow the non-linear processes underlying a supercontinuum to provide a desirable spectrum. This length commonly depends on the shape of the pulses as shorter fiber is commonly sufficient for shorter pulses. In one embodiment the non-linear fiber have a length of 1 cm or longer, such 10 cm or longer, such 1 m or longer, such 5 m or longer, such as 8 m or longer, such as 10 m or longer.

In one embodiment the non-linear microstructured fiber is 500 m or less, 100 m or less, 50 m or less, such as 30 m or less, such as 10 m or less.

Figure 1:
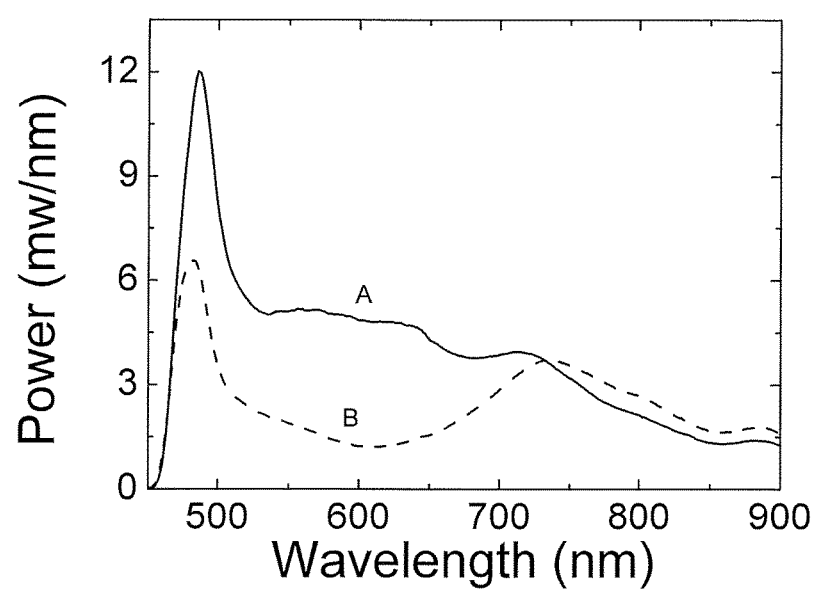
FIG. 1 shows a part of a typical supercontinuum spectra in initial operation of a prior art microstructured optical fiber (A) and after 35 hours of operation (B) all else equal. The reduction in the visible spectrum testifies to the degradation of the fiber.
Figure 2:
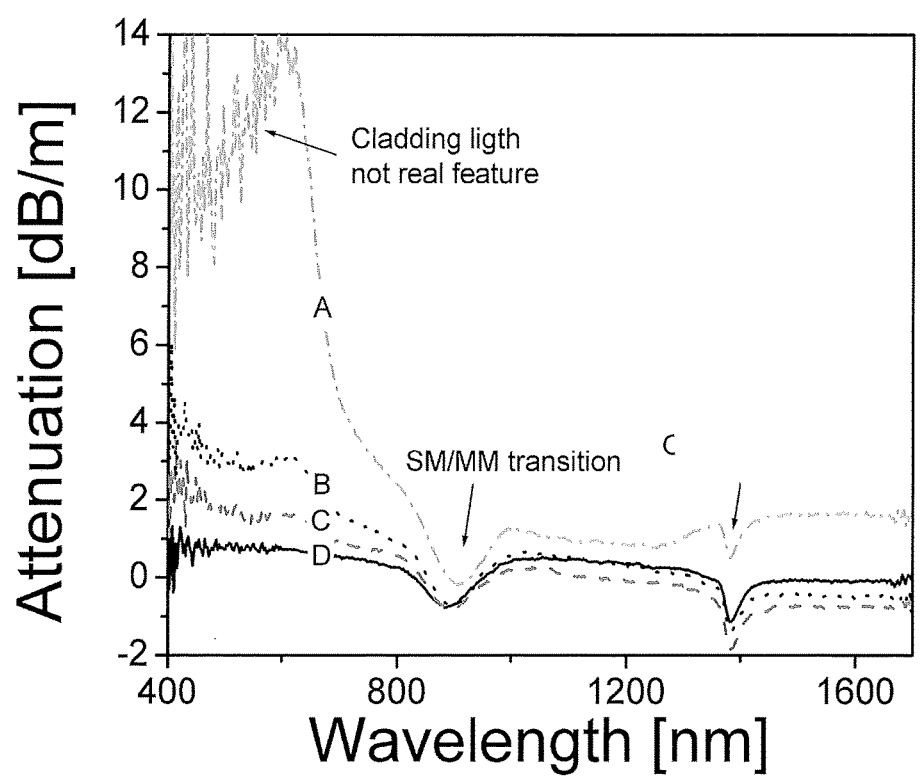
FIG. 2 shows measured attenuation for a prior art microstructured nonlinear fiber operated for 35 hours as a function of the position of the fiber.
Figure 3:
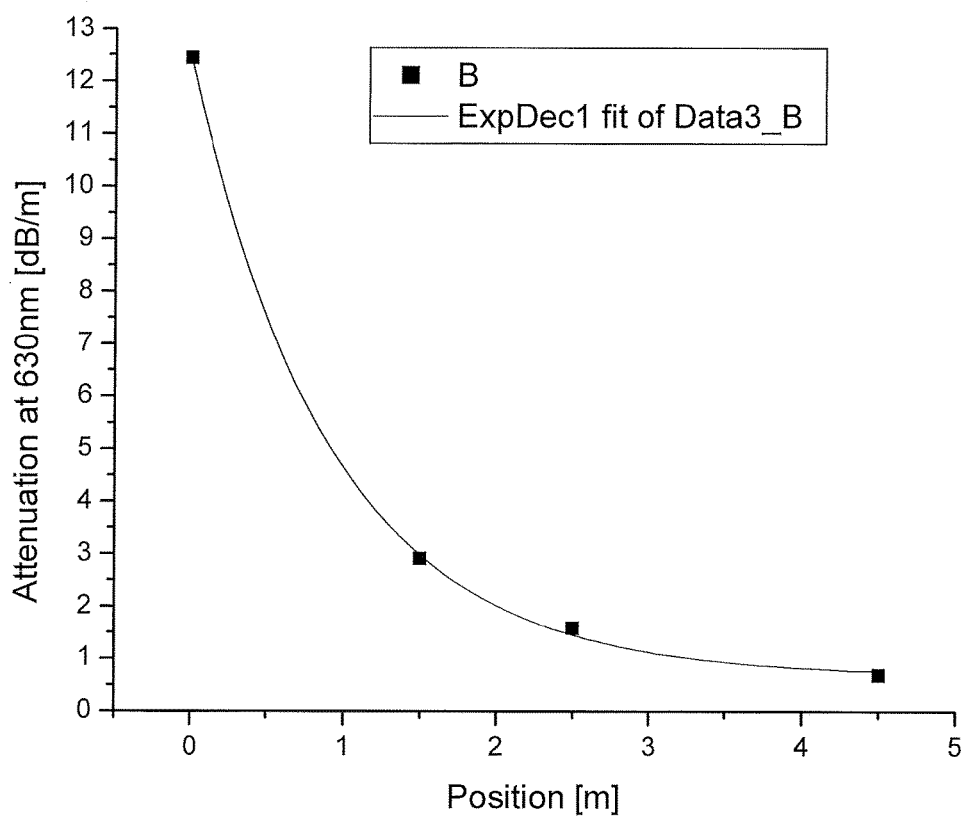
FIG. 3 shows 633 nm absorption as function of position in the microstructured nonlinear fiber, where position means length from the entrance of the pump light.

FIG. 1 shows typical supercontinuum spectra in initial operation of a prior art microstructured optical fiber (A) and after 35 hours of operation (B) all else equal. The reduction in the visible portion of the spectrum extending from about 450 nm to about 750 nm testifies to the degradation of the fiber. The phenomenon is investigated further by the measurements shown in FIG. 2 showing attenuation for the prior art microstructured nonlinear fiber operated for 35 hours as a function of the position of the fiber from the entrance of the pump light. A is measured through the first 3 m of the nonlinear fiber (NL-fiber), B is through 3-4 m, C through 4-5 m and D through 5-7 m. The curves are obtained by subtracting a spectrum obtained with a 7 m long reference non-linear fiber which has not been operated with high power for a longer duration of time. Very large absorption is observed in the visible part of the spectrum due to the degradation of the fiber. The dip at 0.9 µm and 1.4 µm likely stems from the single-mode cut-off for the microstructured nonlinear fiber and differences in O—H peak absorption for the microstructured nonlinear fiber and the reference fiber, respectively. If the degradation is caused by interaction with the relatively high peak powered pump pulse, then the degradation is expected to be larger closer to the pump laser where the peak power is maximal. As the pump pulses travel through the fiber their average power decreases due to attenuation. Furthermore, non-linear effects will tend to broaden the pulse to reduce the peak power of the pulses along the fiber. Therefore less degradation is expected along the fiber further from the injection of the pump pulses. This tendency is seen in this example as the absorption drops as the fiber sections are taken from parts which were operated further and further from the pump. This trend is also found in FIG. 3 showing that measurements of the absorption at 633 nm as a function of distance from the entrance of the pump light fit well to an exponential.

Figure 4:
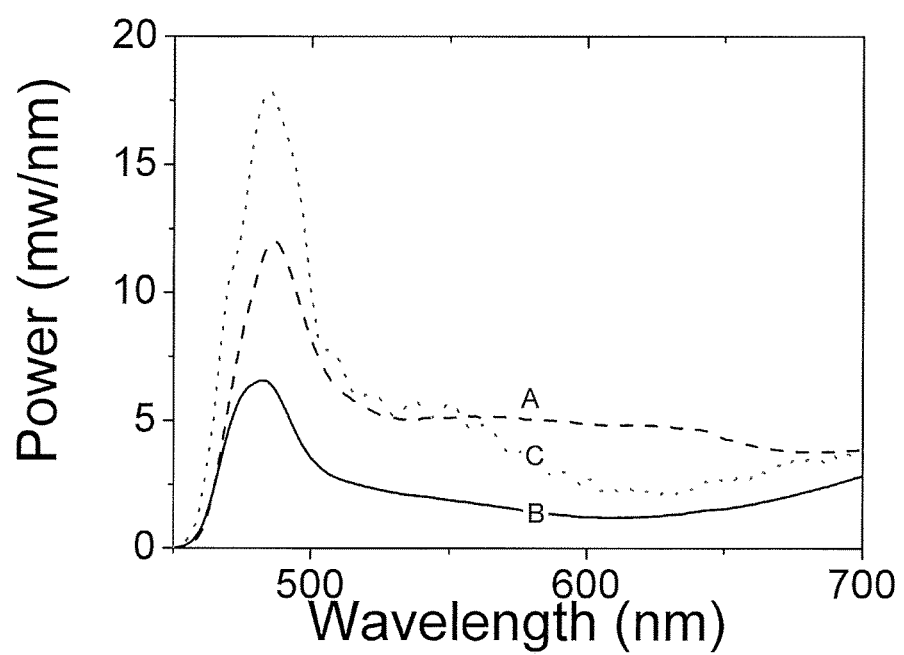
FIG. 4 shows the initial visible supercontinuum spectra (A), after 35 hours of operation where the visible dip is observed (B) and again after heating the fiber to 250° C. (C)

FIG. 4 shows the supercontinuum spectra in the beginning of the experiment (A), after 35 hours were the visible dip is observed (B) and again after heating the fiber to 250° C. (C). The heating seems to partly regenerate the fiber. The inventors hypothesize that the regeneration of the fiber may be an indicator of the pump light altering the structure of at least a part of the glass. Allowing the glass to reach a higher temperature may allow the glass to resettle causing it to at least partly regenerate.

Figure 5:
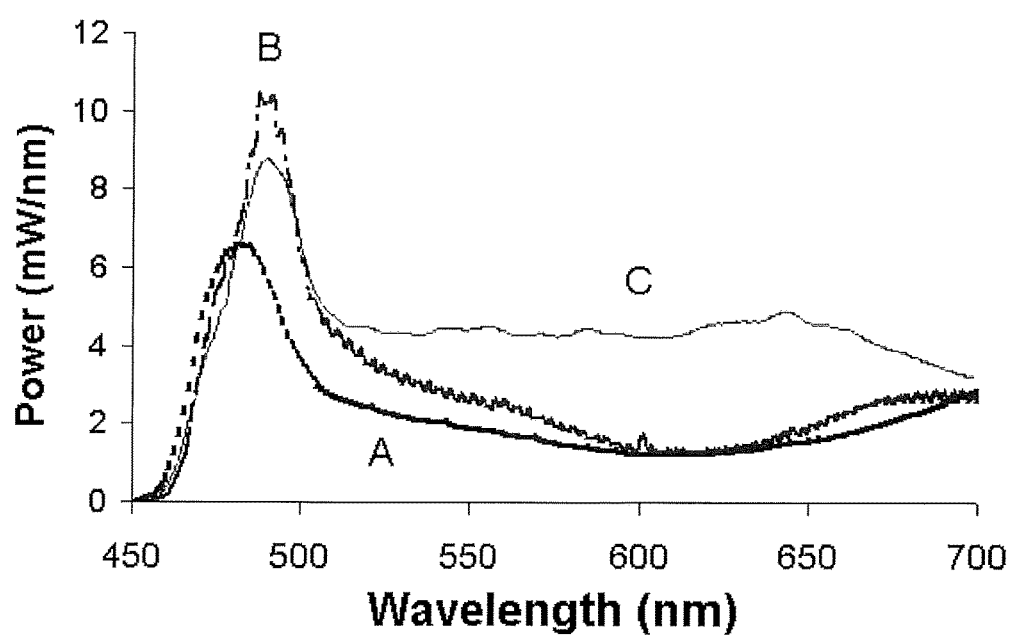
FIG. 5 shows supercontinuum spectra after 35 hours of operation (A) where a visible dip is observed and again after heating the fiber to 250° C. (B) and after the fiber has been deuterium loaded and annealed (C)

FIG. 5 shows supercontinuum spectra after 35 hours (A) where a visible dip is observed and again after heating the fiber to 250° C. (B) and after the fiber has been deuterium loaded and subsequently annealed (C). The deuterium loading clearly regenerated the fiber and the spectrum resembles the initial spectrum (see FIG. 4) without any visible dip in the spectrum.

Figure 6:
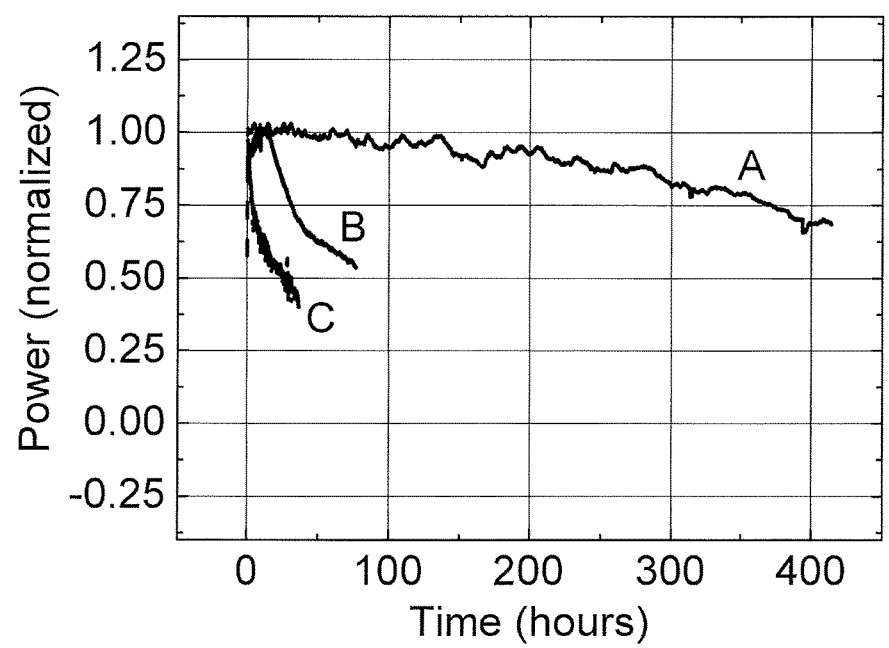
FIG. 6 shows measured visible power as function of time for microstructured nonlinear fibers deuterium loaded at 160 C (A), at 80 C (B) and not deuterium loaded (C)

FIG. 6 shows measured visible power of a supercontinuum source as function of time for 3 pieces of identical microstructured nonlinear fibers deuterium loaded at 160 C (A), at 80 C (B) and not deuterium loaded (C). The lifetime of the deuterium loaded fibers is increased by at least 2 orders of magnitude compared to unloaded fibers. All fibers are loaded at 100 bar pressure with 100% deuterium.

Figure 7:
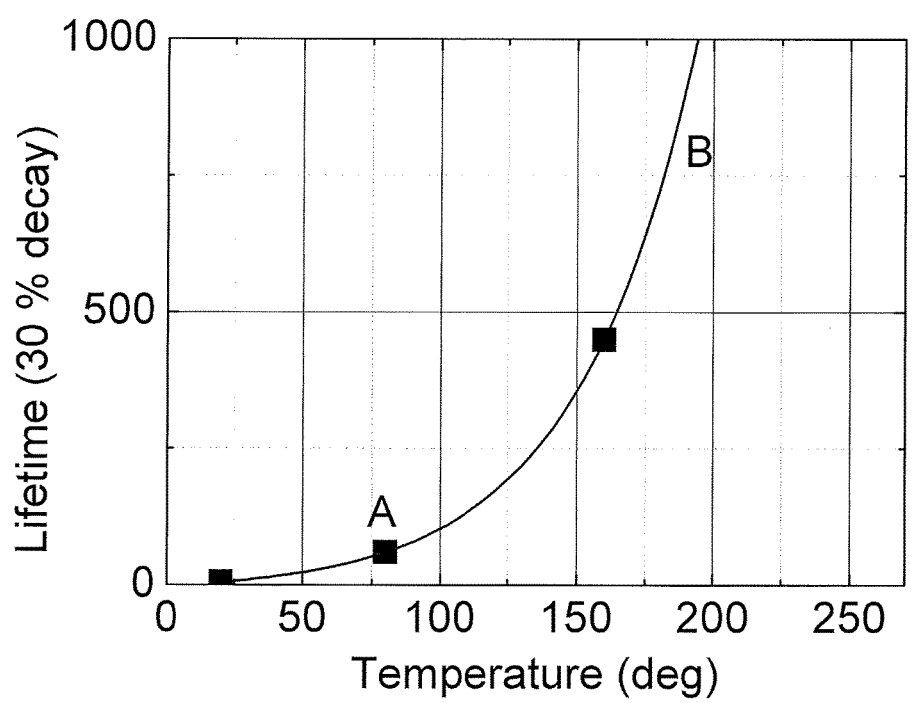
FIG. 7 shows extracted lifetime as function of three different deuterium loading temperatures (A) and an exponential fit to the measurements (B)

FIG. 7 shows lifetime extracted from FIG. 6 as a function of deuterium loading temperature (A) and an exponential fit to the measurements (B). In this example the lifetime was defined as the time where the visible power has decreased 30%. Depending on the application the lifetime may be defined as where the visible power has decreased by more than 40%, such as more than 50%, such as more than 70%, such as more than 80%, such as more than 90%. Visible light may in the context be defined as an integral of light in the range 0.4 to 0.7 µm. Alternatively, one or more wavelength values may be specified such as the power at 650 nm and/or at 633 nm. As discussed above these results may indicate that the lifetime of the fiber increases exponentially with loading temperature, at least for the temperatures applied here and that loading at increased temperature may be advantageous as long as practical factors such as the temperature tolerance of the coating is considered.

Figure 8:
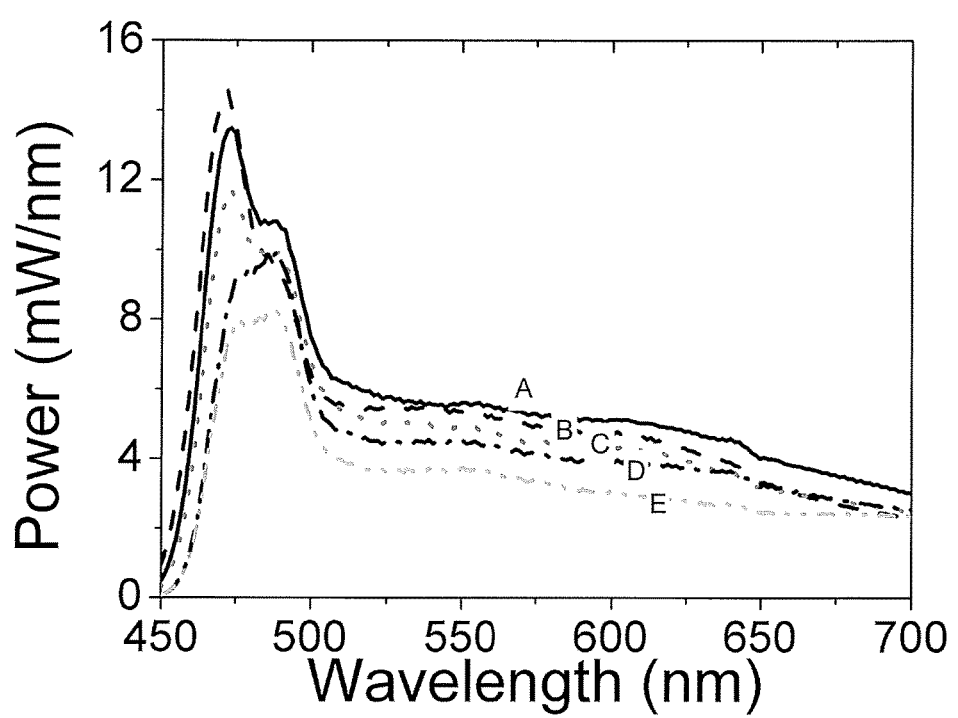
FIG. 8 shows measured spectra for a deuterium loaded microstructured nonlinear fiber after 0 hours (A), 188 hours (B), 260 hours (C), 305 hours (D) and 450 hours (E) of operation.

FIG. 8 shows measured spectra for a deuterium loaded microstructured nonlinear fiber after 0 hours (A), 188 hours (B), 260 hours (C), 305 hours (D), and 450 hours (E). The prominent broad dip for the non-loaded microstructured fiber in the visible spectrum from 0.4 to 0.7 µm is no longer observed. In addition to increasing the lifetime of the microstructured nonlinear fiber the deuterium loading has also shown in this embodiment to significantly alter the spectral changes of the fiber under operation compared to unloaded fibers. Relative to an unloaded fiber the degradation is no longer observed as a dip in the visible spectrum, but as a broadening of the long wavelength peak around 475 nm and a slow overall decrease of visible power.

Figure 9:
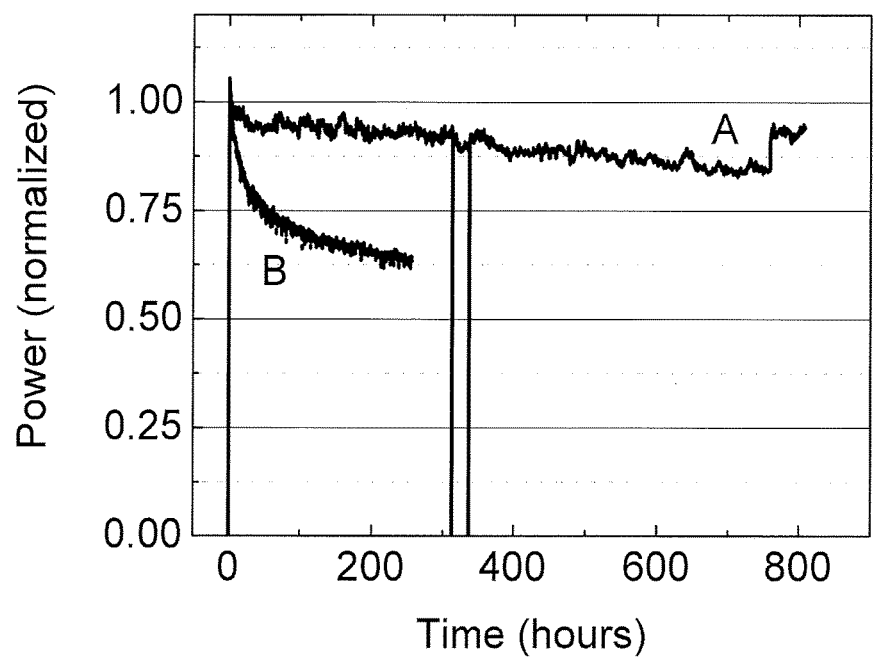
FIG. 9 shows measured visible power as function of time for microstructured nonlinear fibers with less glass impurities compared to the previous figures.

FIG. 9 shows measured visible power as function of time for microstructured nonlinear fibers with less glass impurities for a Deuterium loaded (A) and unloaded (B) fiber. Again the lifetime of the deuterium loaded fiber (A) is significantly increased compared to the unloaded fiber (B). The increase in output power for the deuterium loaded fiber after 750 hours is due to an increase in pump power. Compared to FIG. 5 the lifetime is significantly extended indicating that the lifetime may also depend on the glass impurity level.

Figure 11:
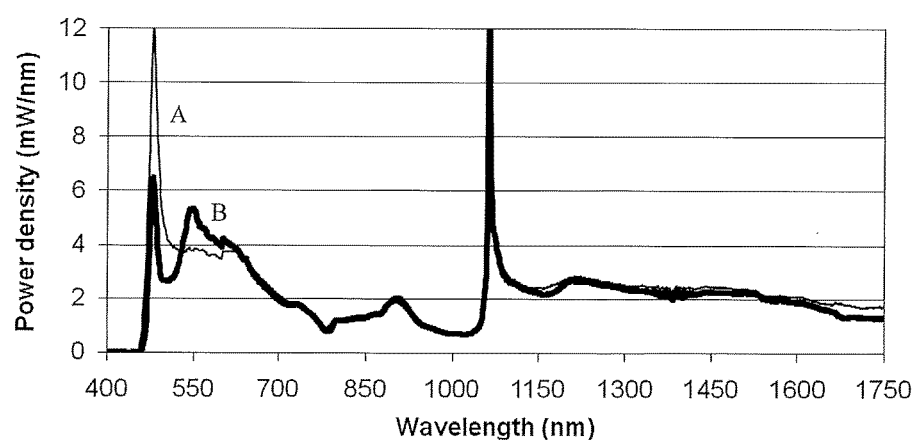
FIG. 11 shows one example of spectra obtained from a supercontinuum light source comprising a non-linear microstructured fibre according to the invention. The spectra are an initial spectrum (A) and a spectrum after a 160 hour operation (B)

FIG. 11 shows one example of spectra obtained from a supercontinuum light source comprising a non-linear microstructured fibre according to the invention. The shown spectra are an initial spectrum (A) and a spectrum after a 160 hours of operation (B). It has been observed that in many of the embodiments of the invention the spectrum shows a reduction in a peak at short wavelengths, commonly around 480 nm, whereas a peak rises from the remaining spectrum around 550 nm in the present embodiment. This peak around 550 nm has not been observed for supercontinuum light sources comprising an unloaded non-linear microstructured fiber as evident from the other figures.

Figure 12:
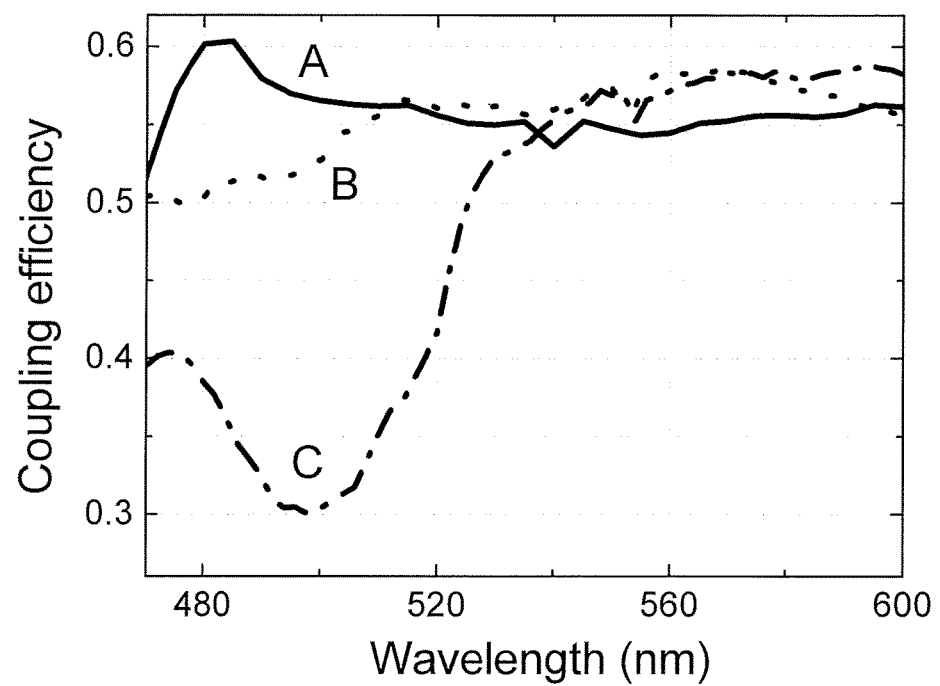
FIG. 12 shows the coupling efficiency spectra from a supercontinuum light source according to the invention to a single mode fiber. The spectra are an initial spectrum (A), and spectra after a 273 hours (B) and 535 hours of operation (C). The microstructured fiber has been annealed for 4 hours at 80 C at a pressure of a standard atmosphere.

In one embodiment of a supercontinuum light source according to the invention it has been observed that the increase in output power around 550 nm shown in FIG. 11 occurs simultaneously with a decrease in spatial mode quality of the output light at wavelengths lower than about 550 nm, i.e. the light is increasingly multimoded. This decreased beam quality may be identified in many ways, e.g. by measuring the coupling efficiency to a single-mode fiber or by measuring the M-square value. FIG. 12 shows the coupling efficiency from a super continuum source according to the invention to a single mode fiber as a function of wavelength for 0, 273 and 535 hours of operation. The measurement uncertainty is a few percent and thus the coupling efficiency above 550 nm is within the measurement uncertainty unchanged with time. However, below 550 nm the coupling efficiency drops with time.

Figure 13:
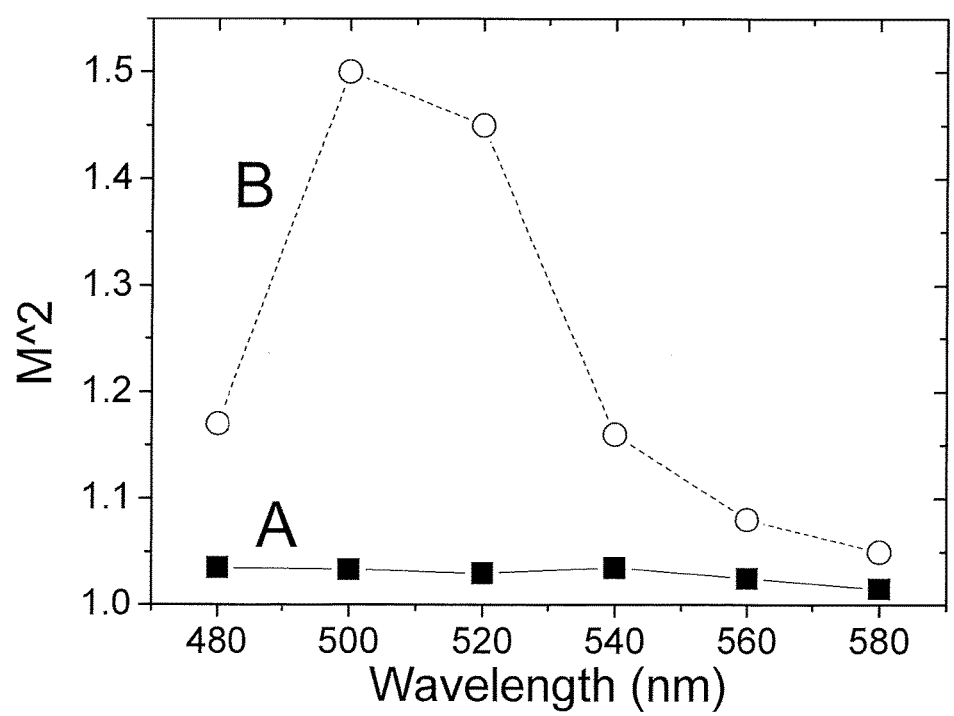
FIG. 13 shows $M^2$ measurements vs. wavelength for a supercontinuum light source according to the invention. The microstructured fiber has been annealed for 4 hours at 160

FIG. 13 shows the $M^2$ spectra for a supercontinuum source according to the invention. The spectra are an initial spectrum (A) and a spectrum after 3500 hours of operation where the fiber has degraded in the visible region (B). Notice that the time until degration occurs is much longer than in FIG. 12. The difference between FIGS. 13 and 12 is that in FIG. 13 the nonlinear fiber has been annealed for 4 hours at 160 C in an atmosphere of nitrogen prior to use, whereas in FIG. 12 the nonlinear fiber has been annealed for 4 hours at 80 C in a standard atmosphere prior to use.

In one embodiment the time of operation until the described change around 550 nm occurs depends on the anneal conditions of the fiber used to generate the super continuum, such as a microstructured or standard nonlinear fiber. In one embodiment increased temperature of the anneal extends this time of operation before such changes around 550 nm are observed. In one embodiment the time during which the fiber is annealed has a similar effect. In one embodiment this correlation indicates that too much residual hydrogen or deuterium in the fiber may affect said time of operation. In one embodiment the fiber is annealed after subsequent irradiation. In one embodiment this has the effect of allowing residual hydrogen and/or deuterium to provide a benefit during subsequent irradiation and subsequently to that removing at least part of the residual hydrogen/deuterium. In one embodiment the fiber is annealed prior and post subsequent irradiation.

As the light below about 550 nm becomes more multimoded more optical energy may be coupled to these higher order modes. In one embodiment the fiber is coiled to strip these higher order modes for wavelengths of less than about 550 nm and/or to prevent coupling to such higher order modes. In one embodiment the fiber comprises a chirally coupled core to strip these higher order modes for wavelengths of less than about 550 nm and/or to prevent coupling to such higher order modes. FIG. 14 shows the output spectrum of a supercontinuum light source according to the invention after 3200 hours of operation. The microstructure fiber has been annealed for 4 hours at 160 C in an atmosphere of nitrogen prior to use. The spectra A is for a normal supercontinuum source, whereas in B the nonlinear fiber is coiled with a radius of 20 mm. It is observed that the coiling decreases the output power at the 550 nm peak and furthermore increases the short wavelength peak around 480 nm as well as restores the $M^2$ value.

The inventors have surprisingly found that in one embodiment a relatively narrow coil is required but also that such a coil may in one embodiment function even when the fiber is a micro structured fiber, which would otherwise be considered sensitive to such mechanical stress. In one embodiment at least part of the fiber is coiled with a minimum diameter R where R is less than or equal to 40 mm, such as less than or equal to 30 mm such as less than or equal to 25 mm, such as less than or equal to 20 mm, such as less than or equal to 15 mm, such as less than or equal to 10 mm, such as less than or equal to 5 mm. In a coil the radius of each winding may vary e.g. depending on the winding method and whether the winding is the inner most winding or not. In this case, the minimum radius R refers to the radius of the winding with the smallest radius.

In one embodiment the position of the coil relative to where the pump light is injected affects the efficiency of the coil to prevent the drop in average optical output power). Closer to the injection of the pump light the peak power of the pump pulse are higher and the formation of the different wavelengths of the output spectrum of the super continuum source may in one embodiment be at least partly related to the position along the fiber.

Accordingly, in one embodiment the fiber has an input end coupled to said pump light source and an output end, wherein said coiling is performed less than 50 cm from the input end, such as less than 40 cm, such as less than 30 cm, such as less than 20 cm, such as less than 10 cm, such as less than 5 cm. To use the stripping effect provided by the coil at a position where specific wavelengths of the output spectrum are generated, the coil may, in one embodiment, cover at least a distance which is more than 5 cm from the input end, such as more than 10 cm from the input end, such as more than 20 cm from the input end, such as more than 30 cm from the input end, such as more than 40 cm from the input end, such as more than 50 cm from the input end, such as more than 70 cm from the input end, such as more than 80 cm from the input end. In one embodiment little of the fiber is required to be coiled to reduce the said degradation at wavelengths below 550 nm. In one embodiment more of the fiber is required to be coiled, such as to prevent the degradation occurring in an uncoiled section of the fiber. In one embodiment more than or equal to 10% of said fiber is coiled, such as more than or equal to 20% of said fiber is coiled, such as more than or equal to 30% of said fiber is coiled, such as more than or equal to 40% of said fiber is coiled, such as more than or equal to 50% of said fiber is coiled, such as more than or equal to 60% of said fiber is coiled such as more than or equal to 70% of said fiber is coiled, such as more than or equal to 80% of said fiber is coiled, such as more than or equal to 90% of said fiber is coiled, such as 100% of the fiber is coiled. In one embodiment one winding is sufficient to prevent the degradation discussed above and/or to strip higher order modes and/or suppress coupling of light from the fundamental mode to higher order modes. However, in one embodiment two or more windings may be required to provide sufficient effect. Accordingly, in one embodiment said coil comprises 1 or more windings, such as 2 or more windings, such as 10 or more windings, such as 25 or more windings, such as 50 or more windings, such as 100 or more windings. In one embodiment the number of required winding decreases with the winding radius. In one embodiment it may be preferable to wind a long section, such as all, of the fiber with a lesser larger radius rather than submit the fiber to the mechanical stress imposed by a smaller radius.

As will be obvious to the skilled person, the detailed effects of increasing and decreasing peaks as well as the region of wavelengths for which the beam quality drops discussed here are exemplary relating to the embodiments. It is clear that one or more of the discussed effects may depend on the overall design of the supercontinuum light source such as pump properties (e.g. wavelength, peak power, pulse energy etc.) and/or fiber (e.g. material, core size, dopants, mode field diameter etc.). Therefore, it should be recognized that increased anneal temperature and/or stripping of higher order modes, such as described above, may have application in any of the embodiments of the invention including the optical fiber as such and making of the same.

In one embodiment lifetime extension is provided by bound deuterium/hydrogen relative to total number of impurities and/or defects in the core and in some application also in the cladding material. Accordingly, in one embodiment the core of the fiber being a solid core (preferably silica) wherein the fraction of bound hydrogen and/or deuterium relative to the total number of impurities and/or defects is more than or equal to 10%, such as more than or equal to 20%, such as more than or equal to 30%, such as more than or equal to 40%, such as more than or equal to 50%, such as more than or equal to 60%, such as more than or equal to 70%, such as more than or equal to 80%, such as more than or equal to 90%, such as more than or equal to 99%, such as more than or equal 99.9%. In this context all compounds in the glass apart from $SiO_2$ are considered impurities.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

Super Continuum Generation in Standard Fibers

In the present context the term standard fiber refers to fibers guiding light in a solid material substantially free of microstructures. Guiding is obtained by total internal reflection at the interface between a core of the fiber and a cladding, so that the refractive index of the core is higher than the refractive index of the cladding. The fiber may comprise multiple cores and/or claddings such as in double clad fibers or panda fibers.

Similarly to microstructured fibers, supercontinuum (SC) generation may be possible in standard fibers provided that suitable nonlinear and dispersion properties are provided.

In one embodiment SC generation is obtained from standard fiber such as a conventional single-mode fiber similar to what was demonstrated by Watt et al., *Generation of*

*supercontinuum radiation in conventional single-mode fibre and its application to broadband spectroscopy*, Appl. Phys. B 90, 47-53 (2008). Here a single mode fiber (SMF28, Corning) is pumped at 1064 nm with 5 ps pulses. In one embodiment an unloaded SMF28 fiber will experience similar degradation to that observed in a microstructured fiber, and this degradation may be prevented, reduced and/or repaired by way of the invention. In one embodiment, increased load time relative to that of a similar microstructured fiber will be beneficial as a standard fiber lacks holes and therefore comprises more material in and/or around the core.

In one embodiment, guiding in the standard fiber is obtained by doping the cladding in order to reduce the refractive index, such as by fluoride. In one embodiment guiding of the standard fiber occurs in undoped silica.

In one embodiment SC is obtained, at least in part, from tapering of the fiber, similarly to what was demonstrated by Lu et al., *Generation of broadband continuum with high spectral coherence in tapered single-mode optical fibers*, Opt. Expr., Vol. 12, No. 2 (2004). Here 100 fs pulses were pumped into the fiber at wavelengths ranging from 780 nm to 920 nm. In one embodiment, a tapered standard fiber will experience similar degradation to that observed in a microstructured fiber and that this degradation may be prevented, reduced and/or repaired by way of the invention.

Optical Power Transport

Optical fibers (standard and microstructured) may be applied to transport optical energy (CW and/or pulsed) in applications such as guiding of surgical and/or therapeutic light, optical sensing, materials processing and measuring technology. Accordingly, in one embodiment an optical fiber is arranged to receive light from a feeding unit and transport said light substantially unchanged. In this context substantially unchanged is taken to mean that the output of the fiber may be substantially calculated by multiplying with a linear transfer function. Substantially calculated is taken to mean that the calculation is accurate within less than 20% deviation, such as less than 10% deviation, such as less than 5% deviation, such as less than 1% deviation. In one embodiment such an optical fiber will experience similar degradation to that observed in a microstructured fiber described above, and that this degradation may be prevented, reduced and/or repaired by way of the invention.

Active Fibers

In one embodiment the fiber according to the invention is an active fiber suitable for providing optical amplification when pumped with excitation light also referred to as pump light. In one embodiment said active fiber forms part of an optical amplifier and in one embodiment said active fiber forms part of a laser, such as forms part of a laser cavity.

In one embodiment a fiber according to the invention forms part of a laser cavity. Even though a laser may operate at a wavelength far from where deterioration is commonly observed (e.g. in the visible range) a tail of absorption may still be present at the operating wavelength. In a laser light may pass the fiber a high number of times before being coupled out. For this, and other reasons, even a small deterioration may affect the performance of the laser. In one embodiment, the gain medium of the laser compensate at least partly for a small change in absorption due to deterioration. In this event, this may result in stable power output relative to the deterioration; however, with an increase in noise, such as an increase in Relative Intensity Noise (RIN).

In one embodiment the fiber forms part of a laser with an operating wavelength higher than 600 nm, such as higher than or equal to 800 nm, such higher than or equal to 1000 nm, such higher than or equal to 1064 nm, such higher than or equal to 1150 nm, such higher than or equal to 1300 nm, such higher than or equal to 1550 nm. For such a fiber an increase in absorption in the visible may occur as a function of operating time, in the absence of loading according to the invention, similar to that occurring in microstructures fiber in supercontinuum generation. As argued above, such absorption may influence the performance of the laser. By way of the invention such problems may be prevented, reduced and/or repaired so that a fiber according to the invention is applied for part of or the entire optical path of the laser. In one embodiment loading is performed in a manner similar to that of the microstructured fiber for supercontinuum or the fiber for transport.

In one embodiment the fiber forms part of an optical amplifier. In optical amplifiers high optical densities may arise, so that one will observe that deterioration causing increased absorption occurs. This may be prevented, reduced and/or repaired by way of the invention so that a fiber according to the invention is applied for part of or the entire optical path of the amplifier. For lasers as well as amplifiers it is within the scope of the invention that the fiber according to invention is active and/or passive fiber.

FIG. 15 is a schematic cross-sectional view of an optical fiber 100 according to an embodiment of the invention. The drawing is not made to scale, and is not intended to illustrate the relative diameters and thicknesses of the core material 110 and the cladding 112. The optical fiber may be a microstructured fiber and include a pattern (not shown in FIG. 15) of holes or doped glass, extending in the longitudinal direction (i.e., into the page) of the optical fiber 100.

The invention claimed is:

1. An optical supercontinuum system comprising an optical fiber and a feeding unit wherein said feeding unit is a pulsed pump light source and is adapted to feed said optical fiber with pulses with a peak power density within said fiber equal to or higher than 10 W/μm$^2$, wherein said optical fiber comprises a core and a cladding, comprising a core material and a cladding material, respectively, at least a part of the core comprising silica, and wherein said fiber is a non-linear microstructured optical fiber, wherein said non-linear microstructured optical fiber comprises hydrogen and/or deuterium.

2. The optical supercontinuum system of claim 1, wherein said core material has a Germanium content of less than or equal to 20 at %.

3. The optical supercontinuum system of claim 1, wherein said feeding unit is adapted to feed said fiber with pulses with a peak power density within said fiber of equal to or higher than 50 W/μm$^2$.

4. The optical supercontinuum system of claim 1, wherein said fiber is adapted to guide light for at least a range of wavelengths $\lambda_{min}$ to $\lambda_{max}$ and has a non-linear parameter $\gamma$ wherein for at least part of said range the product of the wavelength $\lambda$ and the non-linear parameter $\gamma$ is more than or equal to $4 \cdot 10^{-9}$ W$^{-1}$.

5. The optical supercontinuum system of claim 1, wherein said fiber has a lifetime until the absorption of light in the visible has decreased by more than 40%, wherein said lifetime is more than 100 operating hours.

6. The optical supercontinuum system of claim 1, wherein said fiber is adapted to provide a maximum modulation instability gain $\Omega_{max}$ larger than 20.

7. The optical supercontinuum system of claim 1, wherein the core material is undoped.

8. The optical supercontinuum system of claim 1, wherein the microstructured optical fiber has a length of at least 10 cm and comprises a pattern of holes extending lengthwise in the fiber.

9. The optical supercontinuum system of claim 1, wherein the pump light source comprises a mode locked fiber laser.

10. The optical supercontinuum system of claim 1, wherein:
- said core has a Germanium content of less than or equal to 20 at %;
- said fiber is adapted to guide light for at least a range of wavelengths $\lambda_{min}$ to $\lambda_{max}$ and has a non-linear parameter $\gamma$ wherein for at least part of said range the product of the wavelength $\lambda$ and the non-linear parameter $\gamma$ is more than or equal to $4 \cdot 10^{-9}$ $W^{-1}$;
- said fiber is adapted to provide a maximum modulation instability gain $\Omega_{max}$ larger than 20;
- the microstructured optical fiber has a length of at least 10 cm and comprises a pattern of holes extending lengthwise in the fiber;
- the pump light source comprises a mode locked fiber laser; and
- said fiber has a lifetime until the absorption of light in the visible has decreased by more than 40%, wherein said lifetime is more than 100 operating hours.

11. The optical supercontinuum system of claim 1, wherein said non-linear microstructured optical fiber comprises hydrogen and/or deuterium bound to said core material.

12. The optical supercontinuum system of claim 11, wherein said hydrogen and/or deuterium is chemically bound to said core material.

* * * * *